US011369419B2

(12) United States Patent
Mesiwala et al.

(10) Patent No.: US 11,369,419 B2
(45) Date of Patent: Jun. 28, 2022

(54) IMPLANTS FOR SPINAL FIXATION AND OR FUSION

(71) Applicant: Si-Bone Inc., Santa Clara, CA (US)

(72) Inventors: Ali H. Mesiwala, Claremont, CA (US); Frank M. Phillips, Chicago, IL (US); David W. Polly, Edina, MN (US); Phillip J. Singer, Bowling Green, KY (US); Jeffrey B. Phelps, North Richland Hills, TX (US); Derek P. Lindsey, San Jose, CA (US); Patrick Kahn, Livermore, CA (US); Nikolas F. Kerr, Milpitas, CA (US); Mark A. Reiley, Delray Beach, FL (US); Paul M. Sand, Redwood City, CA (US); Bret W. Schneider, San Jose, CA (US); Scott A. Yerby, Montara, CA (US); Christopher I. Shaffrey, Durham, NC (US); Robert K. Eastlack, La Jolla, CA (US); Juan S. Uribe, Paradise Valley, AZ (US); Isador H. Lieberman, Plano, TX (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

(21) Appl. No.: 16/276,430

(22) Filed: Feb. 14, 2019

(65) Prior Publication Data
US 2020/0261240 A1    Aug. 20, 2020

(51) Int. Cl.
A61B 17/17    (2006.01)
A61F 2/44    (2006.01)
(Continued)

(52) U.S. Cl.
CPC ...... *A61B 17/7055* (2013.01); *A61B 17/7001* (2013.01); *A61B 17/7032* (2013.01);
(Continued)

(58) Field of Classification Search
CPC ............ A61B 17/7001; A61B 17/7032; A61B 17/7055; A61B 17/8685; A61F 2002/30995
See application file for complete search history.

(56) References Cited

U.S. PATENT DOCUMENTS 1,951,278 A    3/1934 Ericsson
2,136,471 A    11/1938 Schneider
(Continued)

FOREIGN PATENT DOCUMENTS

CN    1128944 A    8/1996
CN    1190882 A    8/1998
(Continued)

OTHER PUBLICATIONS

Mauldin et al.; U.S. Appl. No. 16/523,992 entitled "Systems, devices, and methods for joint fusion," filed Jul. 26, 2019.
(Continued)

*Primary Examiner* — Nicholas W Woodall
(74) *Attorney, Agent, or Firm* — Shay Glenn LLP

(57) ABSTRACT

The present invention generally relates to bone implants. More specifically, the present invention relates to bone implants used for the fixation and or fusion of the sacroiliac joint and/or the spine. For example, a system for fusing and or stabilizing a plurality of bones is provided. The system includes an implant structure having a shank portion, a body portion and a head portion. The body portion is coupled to the shank portion and is configured to be placed through a first bone segment, across a bone joint or fracture and into a second bone segment. The body portion is configured to allow for bony on-growth, ingrowth and through-growth. The head portion is coupled to the proximal end of the shank portion and is configured to couple the shank portion to a stabilizing rod. Methods of use are also disclosed.

20 Claims, 31 Drawing Sheets

(51) Int. Cl.
*A61B 17/70* (2006.01)
*A61F 2/28* (2006.01)
*A61F 2/30* (2006.01)
*A61B 17/86* (2006.01)
*A61B 17/02* (2006.01)
*A61F 2/46* (2006.01)

(52) U.S. Cl.
CPC ............ *A61B 17/8685* (2013.01); *A61F 2/28* (2013.01); *A61F 2/30771* (2013.01); *A61F 2/442* (2013.01); *A61F 2/4455* (2013.01); *A61B 17/025* (2013.01); *A61B 17/0218* (2013.01); *A61B 2017/0256* (2013.01); *A61B 2017/8655* (2013.01); *A61F 2/4611* (2013.01); *A61F 2002/2835* (2013.01); *A61F 2002/3085* (2013.01)

(56) References Cited

U.S. PATENT DOCUMENTS

| | | |
|---|---|---|
| 2,243,717 A | 5/1941 | Moreira |
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,556,857 B1 | 4/2003 | Estes et al. |

(56) References Cited

U.S. PATENT DOCUMENTS

| | | |
|---|---|---|
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,142,481 B2 | 3/2012 | Warnick |
| 8,202,305 B2 | 6/2012 | Reiley |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,449,585 B2 | 5/2013 | Wallenstein et al. |
| 8,467,851 B2 | 6/2013 | Mire et al. |
| 8,470,004 B2 | 6/2013 | Reiley |
| 8,475,505 B2 | 7/2013 | Nebosky et al. |
| 8,529,608 B2 | 9/2013 | Terrill et al. |
| 8,608,802 B2 | 12/2013 | Bagga et al. |
| D697,209 S | 1/2014 | Walthall et al. |
| 8,641,737 B2 | 2/2014 | Matthis et al. |
| 8,663,332 B1 | 3/2014 | To et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,858,601 B2 | 10/2014 | Reiley |
| 8,920,477 B2 | 12/2014 | Reiley |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Robling et al. |
| 9,314,348 B2 | 4/2016 | Emstad |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,603,644 B2 | 3/2017 | Sweeney |
| 9,615,856 B2 | 4/2017 | Arnett et al. |
| 9,622,783 B2 | 4/2017 | Reiley et al. |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,820,789 B2 | 11/2017 | Reiley |
| 9,839,448 B2 | 12/2017 | Reckling et al. |
| 9,848,892 B2 | 12/2017 | Biedermann et al. |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| 9,956,013 B2 | 5/2018 | Reiley et al. |
| 9,993,276 B2 | 6/2018 | Russell |

(56) References Cited

U.S. PATENT DOCUMENTS

| | | |
|---|---|---|
| 10,004,547 B2 | 6/2018 | Reiley |
| 10,058,430 B2 | 8/2018 | Donner et al. |
| 10,166,033 B2 | 1/2019 | Reiley et al. |
| 10,188,442 B2 | 1/2019 | Mazel |
| 10,194,962 B2 | 2/2019 | Schneider et al. |
| 10,201,427 B2 | 2/2019 | Mauldin et al. |
| 10,219,885 B2 * | 3/2019 | Mamo ............... A61B 17/0401 |
| 10,258,380 B2 | 4/2019 | Sinha |
| 10,271,882 B2 | 4/2019 | Biedermann et al. |
| 10,335,217 B2 | 7/2019 | Lindner |
| 10,492,921 B2 | 12/2019 | McShane, III et al. |
| 10,531,904 B2 | 1/2020 | Kolb |
| 10,653,454 B2 | 5/2020 | Frey et al. |
| 10,667,923 B2 | 6/2020 | Sullivan et al. |
| 10,729,475 B2 | 8/2020 | Childs |
| 10,743,995 B2 | 8/2020 | Fallin et al. |
| D895,111 S | 9/2020 | Frey et al. |
| 10,758,283 B2 | 9/2020 | Frey et al. |
| 10,758,285 B2 | 9/2020 | Geist et al. |
| 10,799,367 B2 | 10/2020 | Vrionis et al. |
| 10,806,597 B2 | 10/2020 | Soumac et al. |
| 10,842,634 B2 | 11/2020 | Pasini et al. |
| 10,856,922 B2 | 12/2020 | Loke et al. |
| 10,932,838 B2 | 3/2021 | Mehl et al. |
| 10,993,754 B2 | 5/2021 | Kuntz et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0036247 A1 | 2/2006 | Michelson |
| 2006/0036251 A1 | 2/2006 | Reiley |
| 2006/0036252 A1 | 2/2006 | Baynham et al. |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 * | 2/2007 | Matthis ............... A61B 17/866 623/17.11 |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |

(56) References Cited

U.S. PATENT DOCUMENTS

| | | |
|---|---|---|
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevoets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry |
| 2010/0160977 A1 | 6/2010 | Gephart et al. |
| 2010/0168798 A1 | 7/2010 | Clineff et al. |
| 2010/0191292 A1 | 7/2010 | DeMeo et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1* | 7/2012 | Trieu ............... A61B 17/8665 623/17.11 |
| 2012/0226318 A1 | 9/2012 | Wenger et al. |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0296953 A1 | 11/2013 | Mauldin et al. |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0031938 A1 | 1/2014 | Lechmann et al. |

(56) References Cited

U.S. PATENT DOCUMENTS

| | | |
|---|---|---|
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1* | 9/2014 | Vrionis .............. A61B 17/70 606/246 |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288605 A1* | 9/2014 | Mesiwala .............. A61B 17/70 606/279 |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0209094 A1 | 7/2015 | Anderson |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2016/0000488 A1 | 1/2016 | Cross, III |
| 2016/0022429 A1 | 1/2016 | Greenhalgh et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0016630 A1 | 6/2016 | Papangelou et al. |
| 2016/0157908 A1 | 6/2016 | Cawley et al. |
| 2016/0166301 A1 | 6/2016 | Papangelou et al. |
| 2016/0175113 A1 | 6/2016 | Lins |
| 2016/0184103 A1 | 6/2016 | Fonte et al. |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0007409 A1 | 1/2017 | Mauldin et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0049488 A1 | 2/2017 | Vestgaarden |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0202511 A1 | 7/2017 | Chang et al. |
| 2017/0209155 A1 | 7/2017 | Petersen |
| 2017/0216036 A1 | 8/2017 | Cordaro |
| 2017/0224393 A1 | 8/2017 | Lavigne et al. |
| 2017/0246000 A1 | 8/2017 | Pavlov et al. |
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0266007 A1 | 9/2017 | Gelaude et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2018/0104063 A1 | 4/2018 | Asaad |
| 2018/0104068 A1 | 4/2018 | Sack |
| 2018/0104071 A1 | 4/2018 | Reckling et al. |
| 2018/0110624 A1 | 4/2018 | Arnone |
| 2018/0110626 A1 | 4/2018 | McShane, III et al. |
| 2018/0177534 A1 | 6/2018 | Mesiwala et al. |
| 2018/0200063 A1 | 7/2018 | Kahmer et al. |
| 2018/0214192 A1 | 8/2018 | Roby et al. |
| 2018/0228613 A1 | 8/2018 | Jones et al. |
| 2018/0228617 A1 | 8/2018 | Srour et al. |
| 2018/0228621 A1 | 8/2018 | Reiley et al. |
| 2018/0243097 A1 | 8/2018 | Jones et al. |
| 2018/0256351 A1 | 9/2018 | Bishop et al. |
| 2018/0256352 A1 | 9/2018 | Nyahay et al. |
| 2018/0256361 A1 | 9/2018 | Bishop et al. |
| 2018/0280139 A1 | 10/2018 | Jones et al. |
| 2018/0280140 A1 | 10/2018 | Jones et al. |
| 2018/0296363 A1 | 10/2018 | Berry |
| 2018/0303623 A1 | 10/2018 | Shoshtaev |
| 2018/0303624 A1 | 10/2018 | Shoshtaev |
| 2018/0317971 A1 | 11/2018 | Prevost |
| 2018/0368894 A1* | 12/2018 | Wieland .............. A61B 17/866 |
| 2019/0000636 A1 | 1/2019 | Kim et al. |
| 2019/0008562 A1 | 1/2019 | Melton et al. |
| 2019/0076258 A1 | 3/2019 | Black et al. |
| 2019/0076266 A1 | 3/2019 | Trudeau et al. |
| 2019/0083270 A1 | 3/2019 | Milz et al. |
| 2019/0090888 A1 | 3/2019 | Sand et al. |
| 2019/0091027 A1 | 3/2019 | Asaad et al. |
| 2019/0125408 A1 | 5/2019 | Asfora et al. |
| 2019/0133769 A1 | 5/2019 | Tetsworth et al. |
| 2019/0133783 A1 | 5/2019 | Unger et al. |
| 2019/0142606 A1 | 5/2019 | Freudenberger |
| 2019/0150910 A1 | 5/2019 | Jones et al. |
| 2019/0151113 A1 | 5/2019 | Sack |
| 2019/0151114 A1 | 5/2019 | Sack |
| 2019/0183653 A1 | 6/2019 | Gregersen et al. |
| 2019/0231554 A1 | 8/2019 | Bishop et al. |
| 2019/0239935 A1 | 8/2019 | Willis et al. |
| 2019/0254840 A1 | 8/2019 | Gray et al. |
| 2019/0262048 A1 | 8/2019 | Sutika |
| 2019/0262049 A1 | 8/2019 | Tempco et al. |
| 2019/0290441 A1 | 9/2019 | Tong et al. |
| 2019/0298528 A1* | 10/2019 | Lindsey .............. A61B 17/8605 |
| 2019/0298542 A1 | 10/2019 | Kloss |
| 2019/0328546 A1 | 10/2019 | Palagi et al. |
| 2019/0343564 A1 | 11/2019 | Tempco et al. |
| 2019/0343565 A1 | 11/2019 | Tempco et al. |
| 2019/0343566 A1 | 11/2019 | Tempco et al. |
| 2019/0343567 A1 | 11/2019 | Tempco et al. |
| 2019/0343640 A1 | 11/2019 | Donner et al. |

(56) References Cited

U.S. PATENT DOCUMENTS

| | | |
|---|---|---|
| 2019/0343644 A1 | 11/2019 | Ryan et al. |
| 2019/0343645 A1 | 11/2019 | Miccio et al. |
| 2019/0343652 A1 | 11/2019 | Petersheim et al. |
| 2019/0343653 A1 | 11/2019 | McKay |
| 2019/0388131 A1 | 12/2019 | Mehl et al. |
| 2019/0388242 A1 | 12/2019 | Harris et al. |
| 2020/0000595 A1 | 1/2020 | Jones et al. |
| 2020/0022817 A1 | 1/2020 | Crossgrove et al. |
| 2020/0038069 A1 | 2/2020 | Jones et al. |
| 2020/0046512 A1 | 2/2020 | Newman et al. |
| 2020/0100822 A1 | 4/2020 | Lipow |
| 2020/0129214 A1* | 4/2020 | Pepper ............... A61B 17/8625 |
| 2020/0138485 A1* | 5/2020 | Kuwamura ........ A61B 17/8645 |
| 2020/0138492 A1 | 5/2020 | Kavanagh |
| 2020/0170679 A1 | 6/2020 | Sciubba et al. |
| 2020/0246158 A1 | 8/2020 | Bergey |
| 2020/0268525 A1 | 8/2020 | Mesiwala et al. |
| 2020/0345507 A1 | 11/2020 | Reiley |
| 2020/0345508 A1 | 11/2020 | Reiley |
| 2020/0345509 A1 | 11/2020 | Reiley |
| 2020/0345510 A1 | 11/2020 | Reiley |
| 2020/0375750 A1 | 12/2020 | Abbasi et al. |
| 2020/0397491 A1 | 12/2020 | Frey et al. |
| 2021/0107093 A1 | 4/2021 | Tempco |
| 2021/0212734 A1 | 7/2021 | Mesiwala et al. |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 2887899 B1 | 8/2017 |
| EP | 2341852 B1 | 8/2018 |
| EP | 2496162 B1 | 10/2018 |
| EP | 3484387 A1 | 5/2019 |
| EP | 3593745 A2 | 1/2020 |
| EP | 3616634 A1 | 3/2020 |
| EP | 3661441 A1 | 6/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009521990 A | 6/2009 |
| JP | 2009533159 A | 9/2009 |
| JP | 2010137016 A | 6/2010 |
| JP | 2015510506 A | 4/2015 |
| WO | WO97/31517 A2 | 8/1997 |
| WO | WO 01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2009/025884 A2 | 2/2009 |
| WO | WO2009/029074 A1 | 3/2009 |
| WO | WO2010/105196 A1 | 9/2010 |
| WO | WO2011010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2013/000071 A1 | 1/2013 |
| WO | WO2013/119907 A1 | 8/2013 |
| WO | WO2017/147537 A1 | 8/2017 |
| WO | WO2020/168269 A1 | 8/2020 |

OTHER PUBLICATIONS

Reiley et al.; U.S. Appl. No. 16/550,032 entitled "Implants for bone fixation or fusion," filed Aug. 23, 2019.

Mauldin et al.; U.S. Appl. No. 16/552,912 entitled "Fenestrated Implant," filed Aug. 27, 2019.

ACUMED; Acutrak Headless Compressioin Screw (product information); 12 pgs; © 2005; retrieved Sep. 25, 2014 from http://www.rcsed.ac.uk/fellows/lvanrensburg/classification/surgtech/acumed/manuals/acutrak-brochure%200311.pdf.

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Reiley et al.; U.S. Appl. No. 16/237,409 entitled "Implants for bone fixation or fusion," filed Dec. 31, 2018.

Mauldin et al.; U.S. Appl. No. 16/261,393 entitled Integrated Implant,: filed Jan. 29, 2019.

Schneider et al.; U.S. Appl. No. 16/263,971 entitled "Matrix Implant," filed Jan. 31, 2019.

Stuart et al.; U.S. Appl. No. 17/104,753 entitled "Bone stabilizing implants and methods of placement across SI joints," filed Nov. 25, 2020.

Reckling et al.; U.S. Appl. No. 17/116,903 entitled "Sacro-iliac joint stabilizing implants and methods of implantation," filed Dec. 9, 2020.

Schneider et al.; U.S. Appl. No. 17/443,388 entitled "Matrix implant," filed Jul. 26, 2021.

Sand et al.; U.S. Appl. No. 17/447,550 entitled "Systems and methods for decorticating the sacroloac joint," filed Sep. 13, 2021.

* cited by examiner

*(Anterior)*

*(Posterior)*

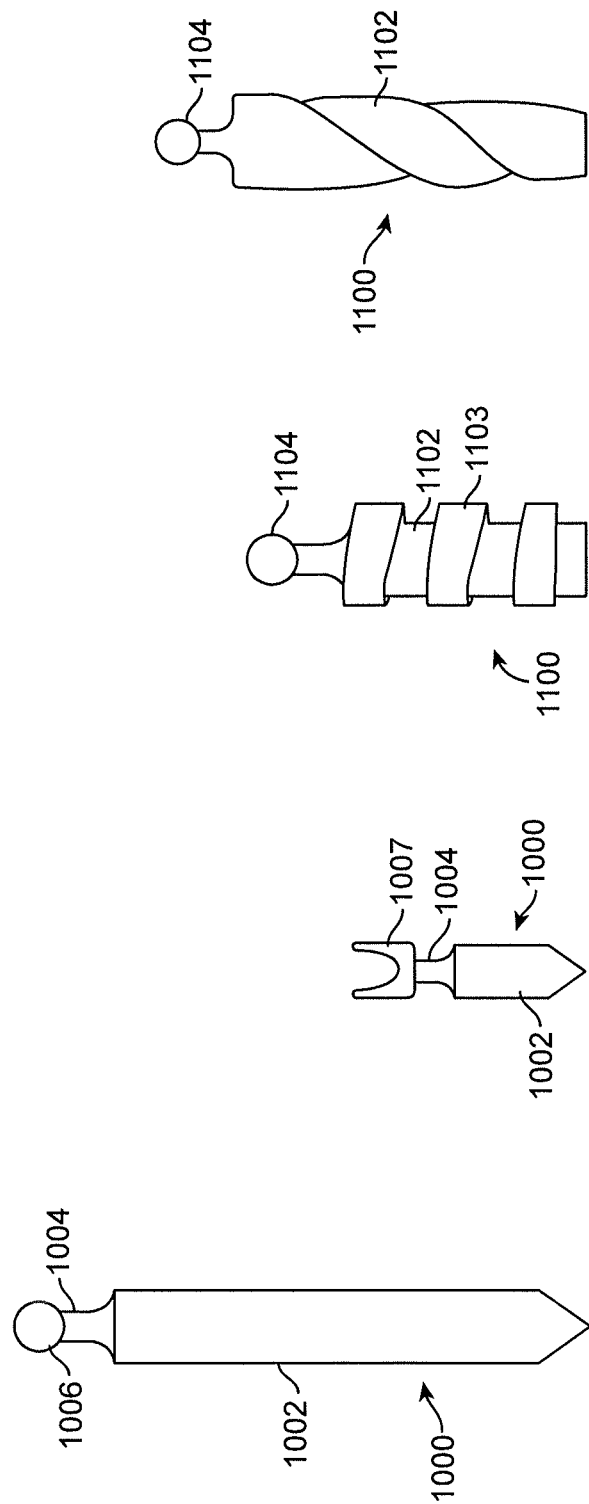

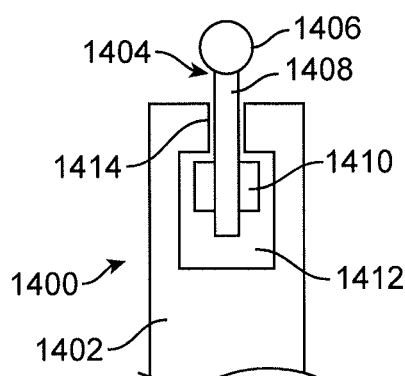
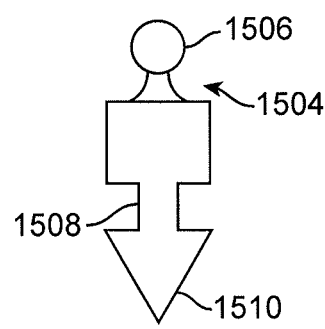
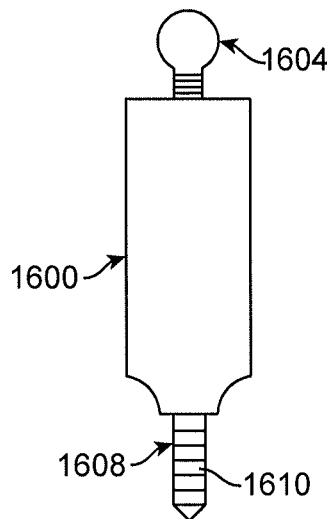
FIG. 14  FIG. 15  FIG. 16
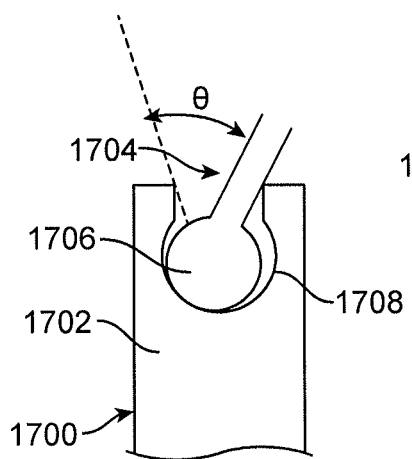
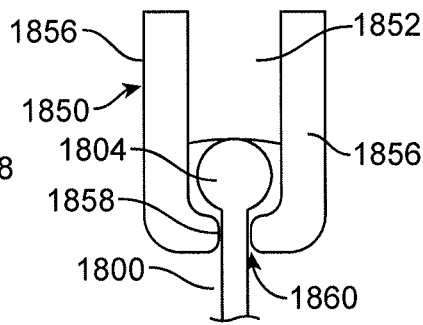
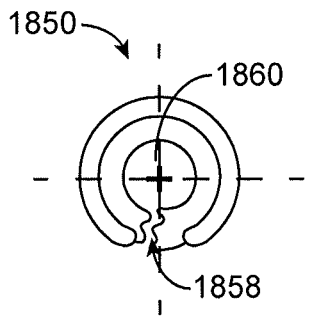
FIG. 17  FIG. 18A  FIG. 18B
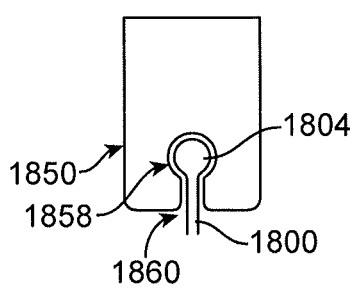
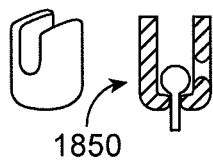
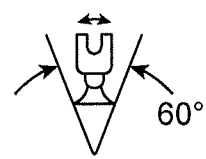
FIG. 18C  FIG. 18D  FIG. 18E Translaminar Lumbar Fusion (Posterior Approach)

Lumbar Facet Fusion (Posterior Approach)

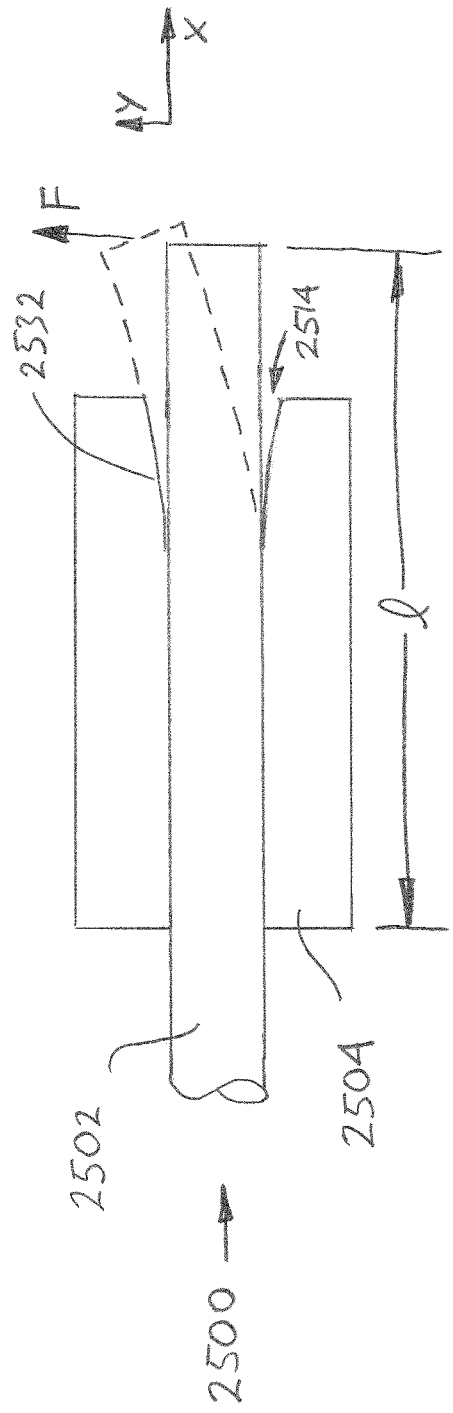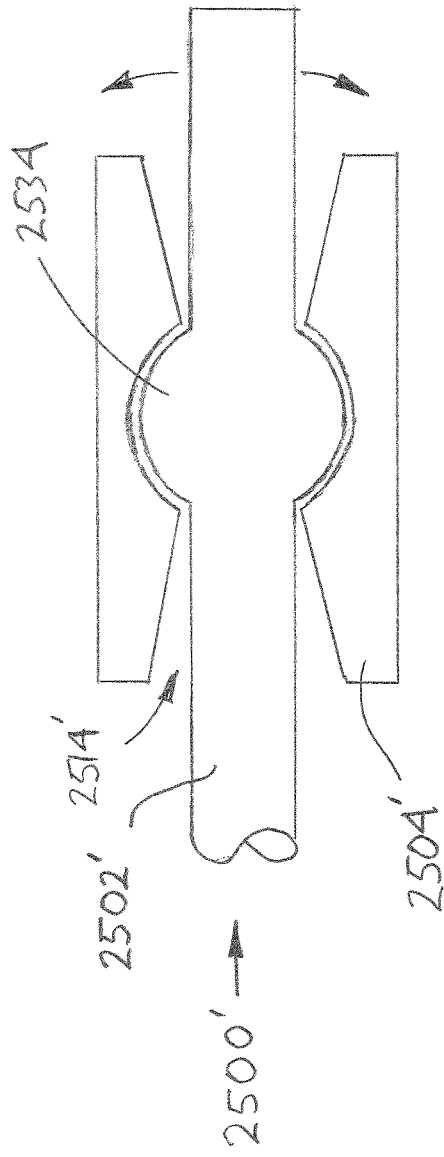
FIG. 25F
FIG. 25G

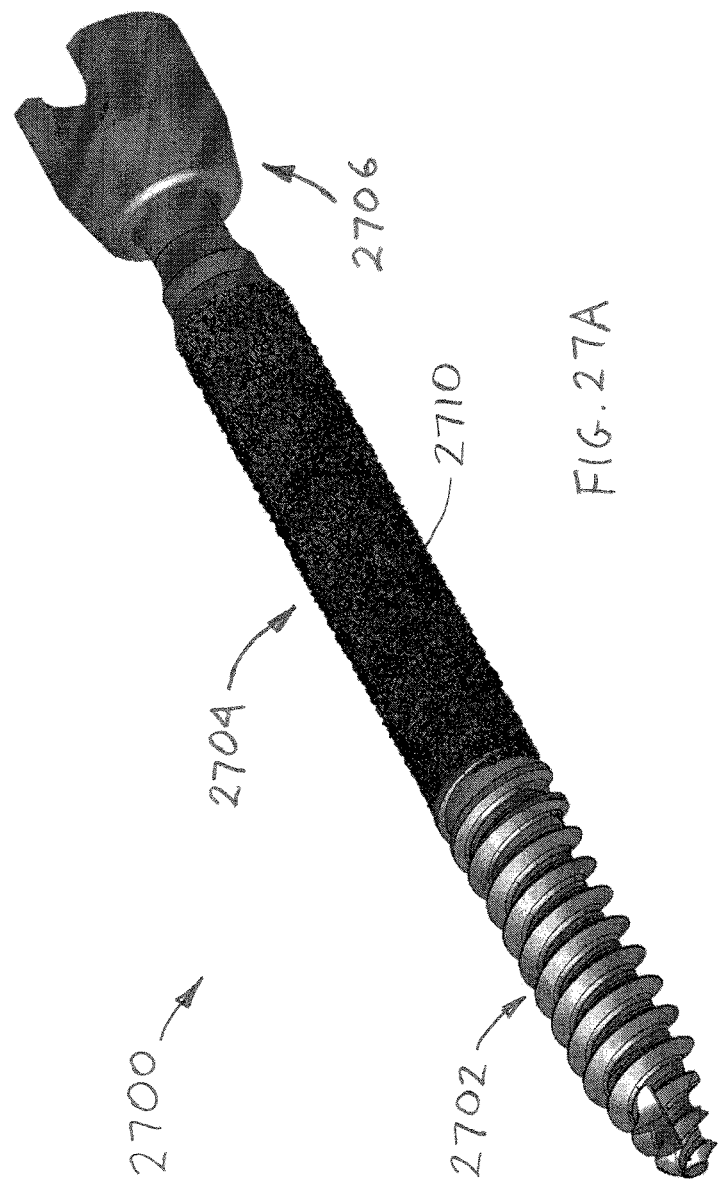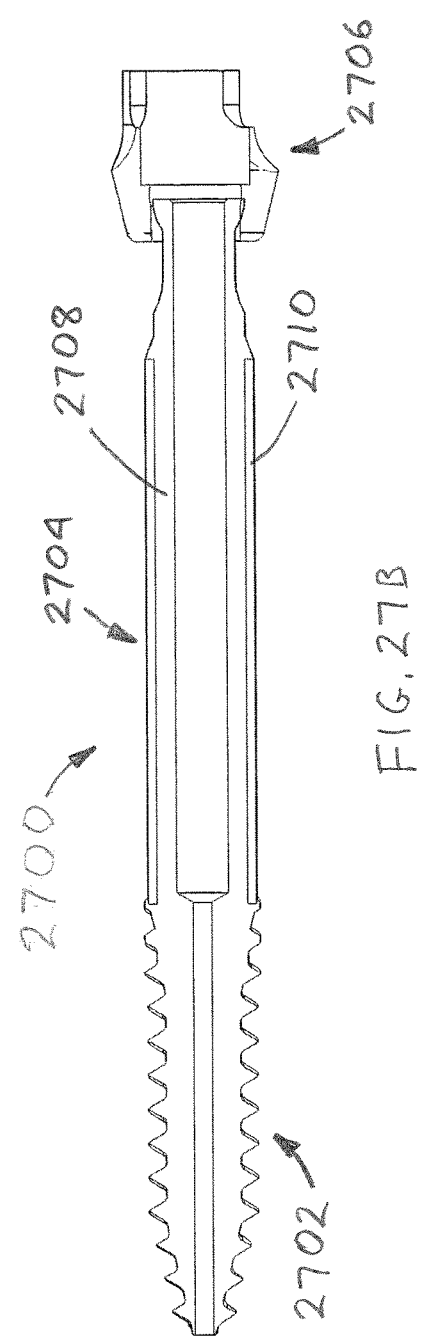

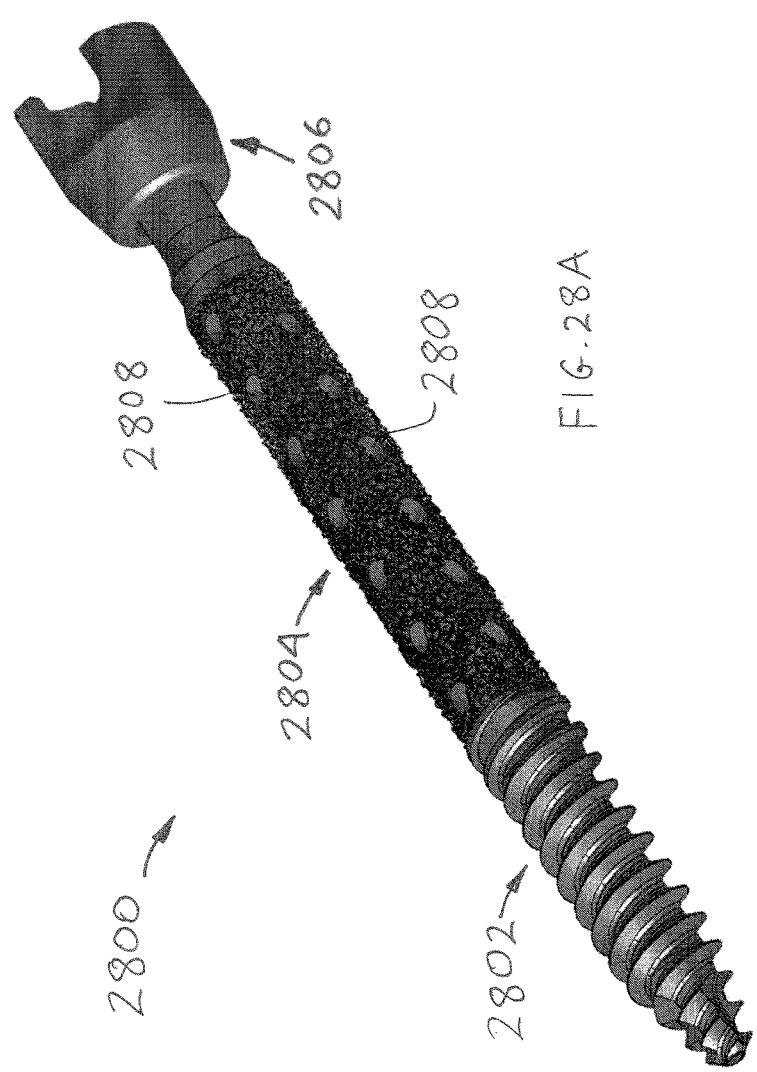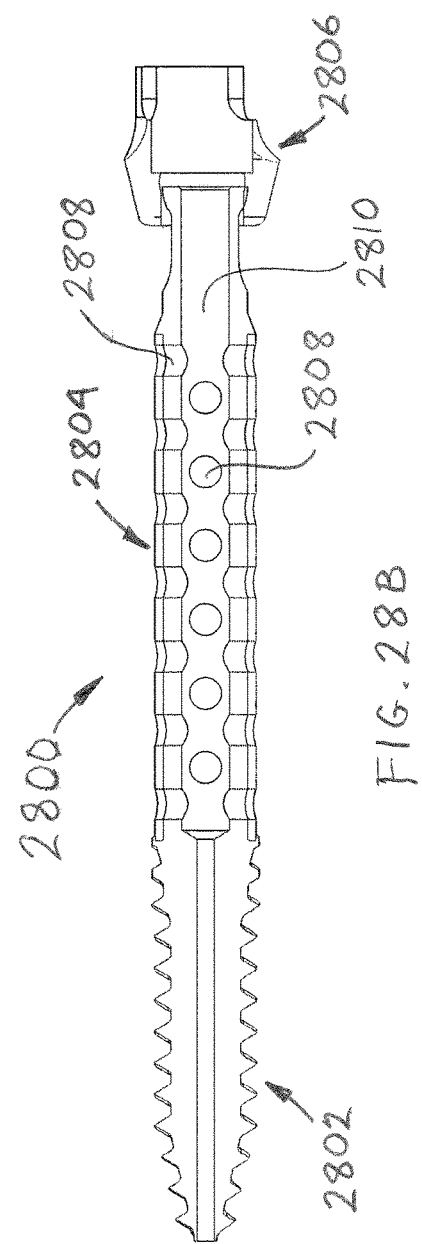

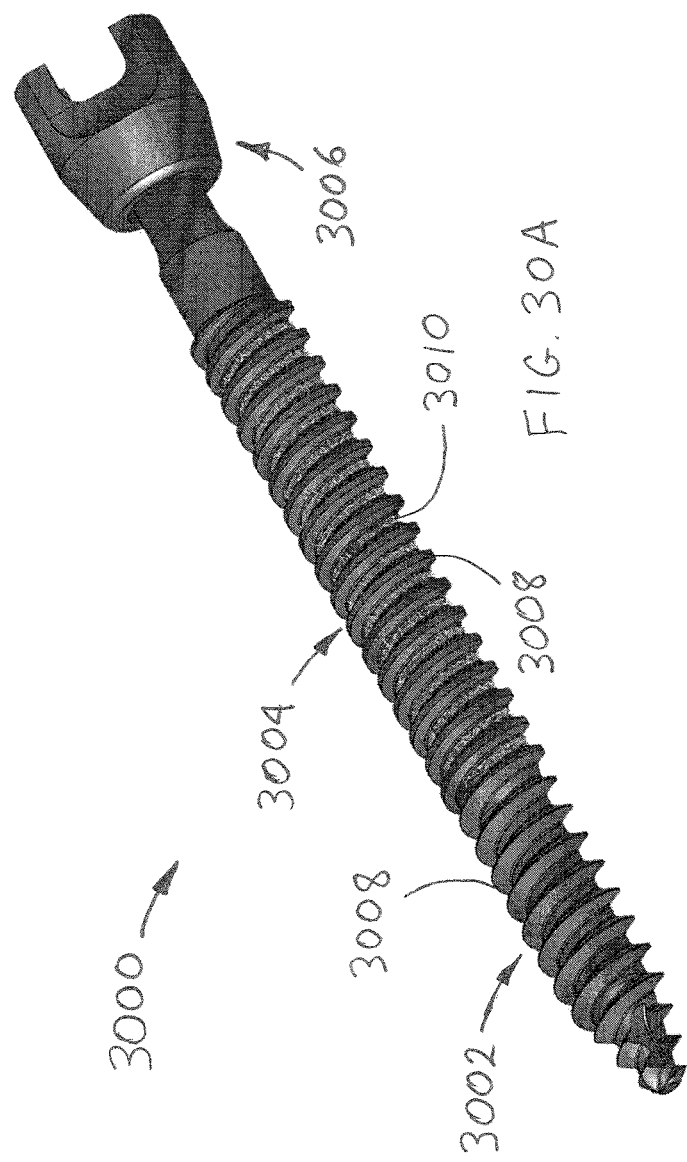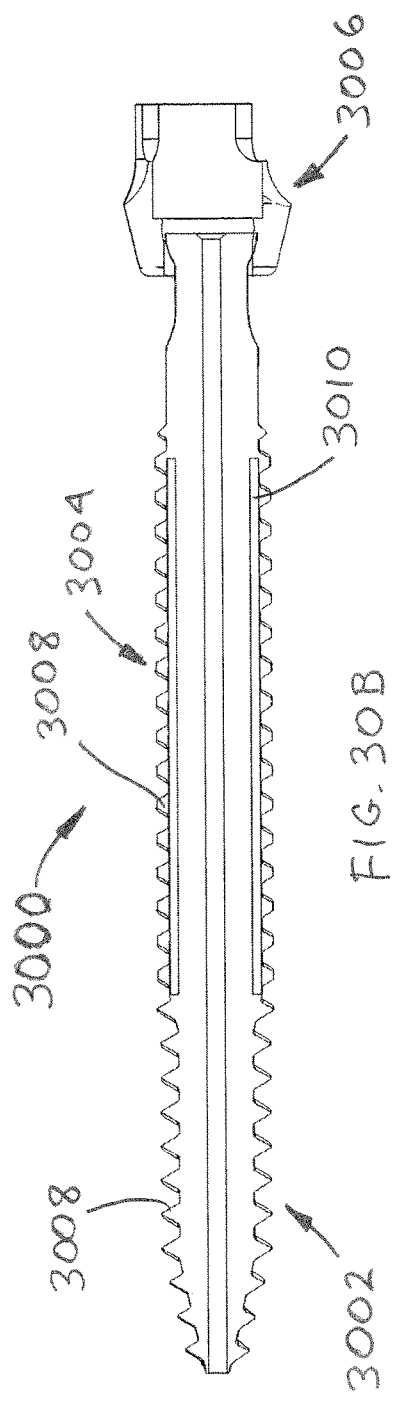

IMPLANTS FOR SPINAL FIXATION AND OR FUSION

INCORPORATION BY REFERENCE

All publications and patent applications mentioned in this specification are herein incorporated by reference to the same extent as if each individual publication or patent application was specifically and individually indicated to be incorporated by reference. For example, this application incorporates by reference in their entireties U.S. Patent Publication No. 2011/0087294, U.S. Patent Publication No. 2011/0087296, U.S. Patent Publication No. 2011/0118785, and U.S. Patent Publication No. 2011/0125268.

FIELD

The present invention generally relates to bone implants. More specifically, the present invention relates to bone implants used for the stabilization, fixation and/or fusion of the sacroiliac joint and/or the spine.

BACKGROUND

Many types of hardware are available both for the fixation of bones that are fractured and for the fixation of bones that are to be fused (arthrodesed).

For example, the human hip girdle is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain.

To relieve pain generated from the SI-Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacroiliac fusion. At the same time the cartilage has to be removed from the "synovial joint" portion of the SI-Joint. This requires a large incision to approach the damaged, subluxed, dislocated, fractured, or degenerative joint.

An alternative implant that is not based on the screw design can also be used to fuse the SI-Joint and/or the spine. Such an implant can have a triangular cross-section, for example, as further described below. To insert the implant, a cavity can be formed into the bone, and the implant can then be inserted into the cavity using a tool such as an impactor. The implants can then be stabilized together, if desired, by connecting the implants with a crossbar or other connecting device.

Therefore, it would be desirable to provide systems, devices and methods for SI-Joint and/or spinal stabilization, fixation and/or fusion.

SUMMARY OF THE DISCLOSURE

The present invention generally relates to bone implants. More specifically, the present invention relates to bone implants used for the stabilization, fixation and or fusion of the sacroiliac joint and/or the spine.

In some embodiments, an implant for use in fusing and or stabilizing a plurality of bones is provided with a shank portion, a body portion and a head portion. The shank portion has a proximal end and a distal end. The body portion is coupled to the shank portion and is configured to be placed through a first bone segment, across a bone joint or fracture and into a second bone segment. The body portion is configured to allow for bony on-growth, ingrowth and through-growth. The head portion is coupled to the proximal end of the shank portion and is configured to couple the shank portion to a stabilizing rod.

In some embodiments of the above implants, the distal end of the shank portion is provided with threads for securing the implant to the second bone segment. In some embodiments, the first bone segment is a sacrum and the second bone segment is an ilium. The body portion may be integral with the shank portion. The body portion may include at least one rectilinear face to prevent rotation. In some embodiments, the body portion has a cross-section transverse to a longitudinal axis that is triangular in shape to prevent rotation. The body portion may include at least one apex to prevent rotation. In some embodiments, the body portion includes a plurality of fenestrations that each communicate with a central lumen of the body portion. The shank portion may include at least one spline that mates with a slot within the body portion to prevent relative rotation between the shank portion and the body portion.

In some embodiments, an implant for use in fusing and or stabilizing a plurality of bones is provided with a shank portion, a body portion and a head portion. The shank portion has a proximal end and a distal end. The body portion is coupled to the shank portion and is configured to be placed into a first bone segment. The body portion is configured to allow for bony on-growth, ingrowth and through-growth. The head portion is coupled to the proximal end of the shank portion and is configured to couple the shank portion to a stabilizing rod.

In some embodiments, the first bone segment is a vertebra, a sacrum or an ilium. The distal end of the shank portion may be provided with threads for securing the implant to the second bone segment. In some embodiments, the body portion is integral with the shank portion. In some embodiments, the body portion includes at least one rectilinear face to prevent rotation. The body portion may have a cross-section transverse to a longitudinal axis that is triangular in shape to prevent rotation. In some embodiments, the body portion includes at least one apex to prevent rotation. The body portion may include a plurality of fenestrations that each communicate with a central lumen of the body portion. In some embodiments, the shank portion includes at least one spline that mates with a slot within the body portion to prevent relative rotation between the shank portion and the body portion. The distal end of the shank portion may be provided with a plurality of bristles to allow the shank portion to be distally inserted into a bone but inhibit proximal removal from the bone.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 5 to 7A and 7B are anatomic views showing, respectively, a pre-implanted perspective, implanted perspective, implanted anterior view, and implanted craniocaudal section view, the implantation of three implant structures for the fixation of the SI-Joint using a lateral approach through the ilium, the SI-Joint, and into the sacrum.

FIGS. 10A and 10B illustrate an embodiment of an implant structure with an integrated head portion.

FIGS. 11A and 11B illustrate embodiments of an implant structure suitable for pedicle screw salvage.

FIGS. 14 and 15 illustrate alternative embodiments of head portions with expandable attachment features.

FIG. 16 illustrates an embodiment of an implant structure with a screw-like head portion that extends completely through the stem portion of the implant structure.

FIG. 17 illustrates an embodiment of the attachment of the head portion to the stem portion of the implant structure using a ball and socket joint.

FIGS. 18A to 18E illustrate the head portion of the implant structure in connection with a tulip structure.

FIG. 25F is a side sectional view schematically showing a portion of the bone implant of FIG. 25A.

FIG. 25G is a side sectional view schematically showing a variation of a portion of the bone implant of FIG. 25A.

FIG. 27A is a perspective view showing an exemplary embodiment of a bone implant having a tulip or coupling device provided at its proximal end.

FIG. 27B is a side sectional view showing the bone implant of FIG. 27A.

FIG. 28A is a perspective view showing an exemplary embodiment of a bone implant having a tulip or coupling device provided at its proximal end.

FIG. 28B is a side sectional view showing the bone implant of FIG. 28A.

FIG. 30A is a perspective view showing an exemplary embodiment of a bone implant having a tulip or coupling device provided at its proximal end.

FIG. 30B is a side sectional view showing the bone implant of FIG. 30A.

DETAILED DESCRIPTION

Figure 1:
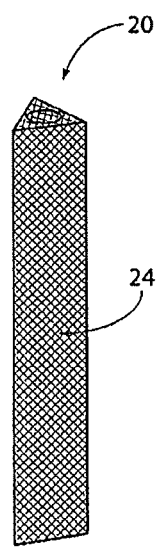
FIG. 1 illustrates an embodiment of an implant structure.
Figure 3:
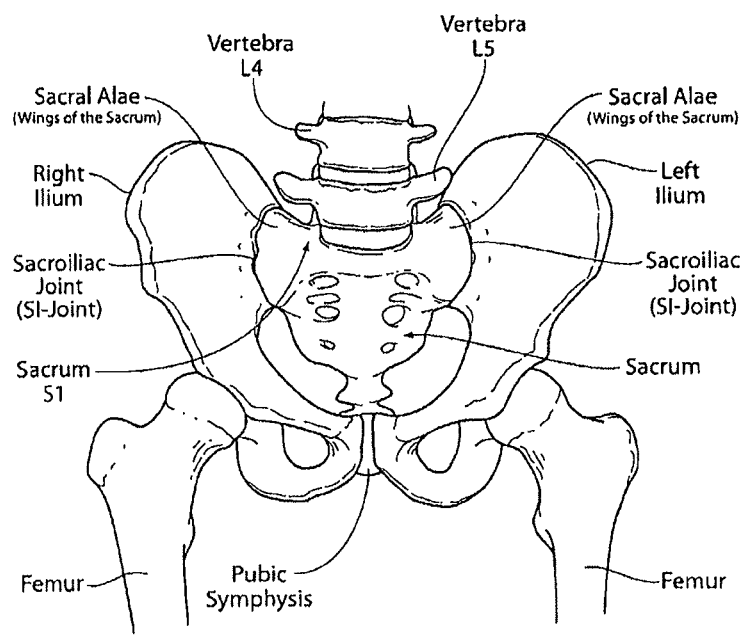
FIGS. 3 and 4 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 4:
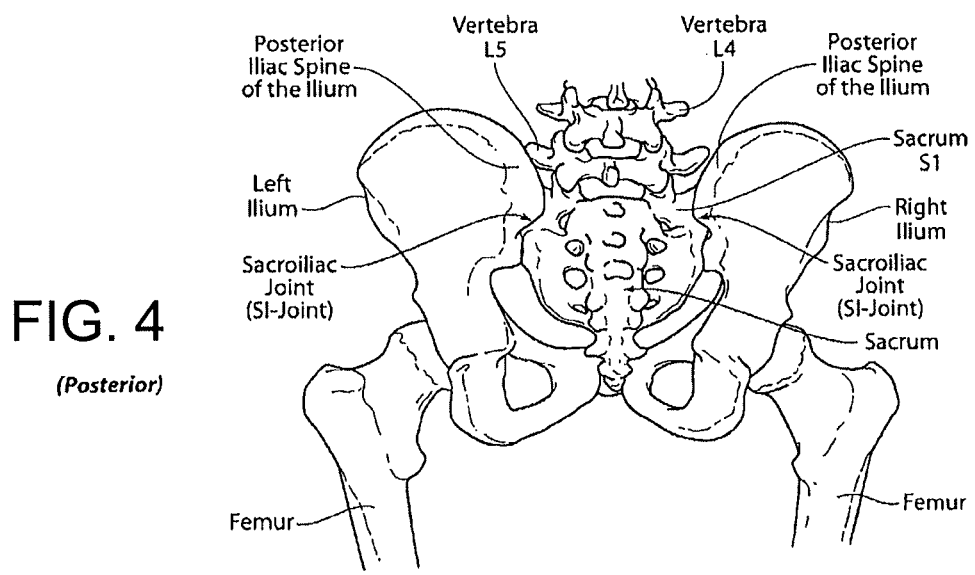

Elongated, stem-like implant structures 20 like that shown in FIG. 1 make possible the fixation of the SI-Joint (shown in anterior and posterior views, respectively, in FIGS. 3 and 4) in a minimally invasive manner. These implant structures 20 can be effectively implanted through the use a lateral surgical approach. The procedure is desirably aided by conventional lateral, inlet, and outlet visualization techniques, e.g., using X-ray image intensifiers such as a C-arms or fluoroscopes to produce a live image feed, which is displayed on a TV screen.

In one embodiment of a lateral approach (see FIGS. 5, 6, and 7A/B), one or more implant structures 20 are introduced laterally through the ilium, the SI-Joint, and into the sacrum. This path and resulting placement of the implant structures 20 are best shown in FIGS. 6 and 7A/B. In the illustrated embodiment, three implant structures 20 are placed in this manner. Also in the illustrated embodiment, the implant structures 20 are rectilinear in cross section and triangular in this case, but it should be appreciated that implant structures 20 of other rectilinear cross sections can be used.

Before undertaking a lateral implantation procedure, the physician identifies the SI-Joint segments that are to be fixated or fused (arthrodesed) using, e.g., the Fortin finger test, thigh thrust, FABER, Gaenslen's, compression, distraction, and diagnostic SI-Joint injection.

Figure 2A:
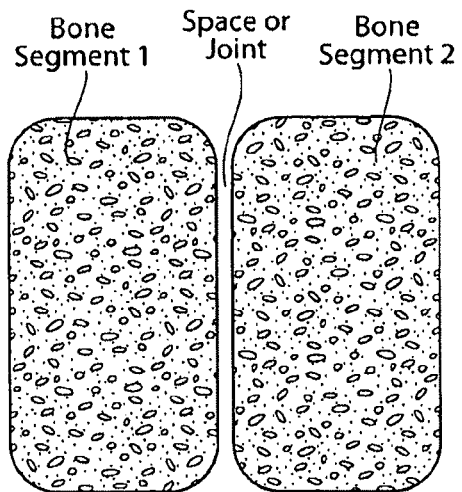
FIGS. 2A-2D are side section views of the formation of a broached bore in bone according to one embodiment of the invention.
Figure 2B:
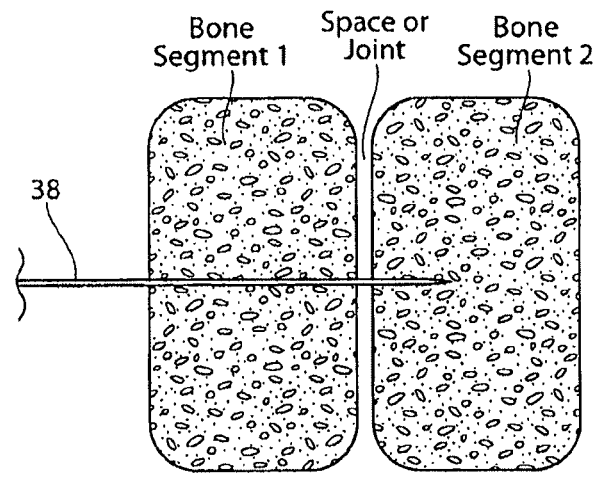

Aided by lateral, inlet, and outlet C-arm views, and with the patient lying in a prone position, the physician aligns the greater sciatic notches and then the alae (using lateral visualization) to provide a true lateral position. A 3 cm incision is made starting aligned with the posterior cortex of the sacral canal, followed by blunt tissue separation to the ilium. From the lateral view, the guide pin 38 (with sleeve (not shown)) (e.g., a Steinmann Pin) is started resting on the ilium at a position inferior to the sacrum end plate and just anterior to the sacral canal. In the outlet view, the guide pin 38 should be parallel to the sacrum end plate and in the inlet view the guide pin 38 should be at a shallow angle anterior (e.g., 15 degrees to 20 degrees off the floor, as FIG. 7B shows). In a lateral view, the guide pin 38 should be posterior to the sacrum anterior wall. In the outlet view, the guide pin 38 should be superior to the first sacral foramen and lateral of mid-line. This corresponds generally to the sequence shown diagrammatically in FIGS. 2A and 2B. A soft tissue protector (not shown) is desirably slipped over the guide pin 38 and firmly against the ilium before removing the guide pin sleeve (not shown).

Figure 2C:
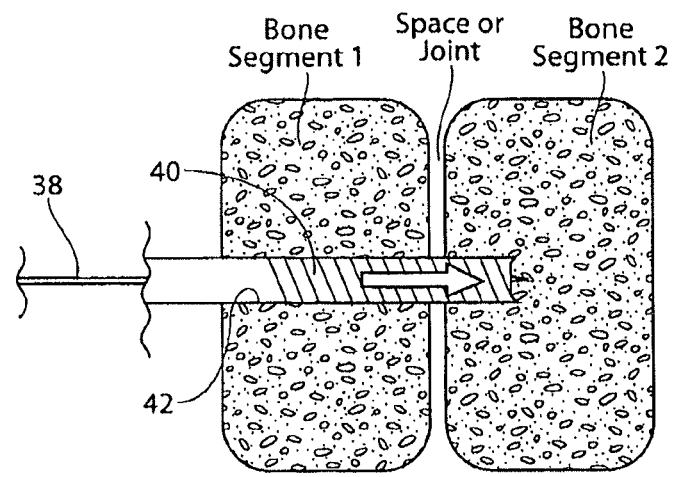

Over the guide pin 38 (and through the soft tissue protector), the pilot bore 42 is drilled in the manner previously described, as is diagrammatically shown in FIG. 2C. The pilot bore 42 extends through the ilium, through the SI-Joint, and into the S1. The drill bit 40 is removed.

Figure 2D:
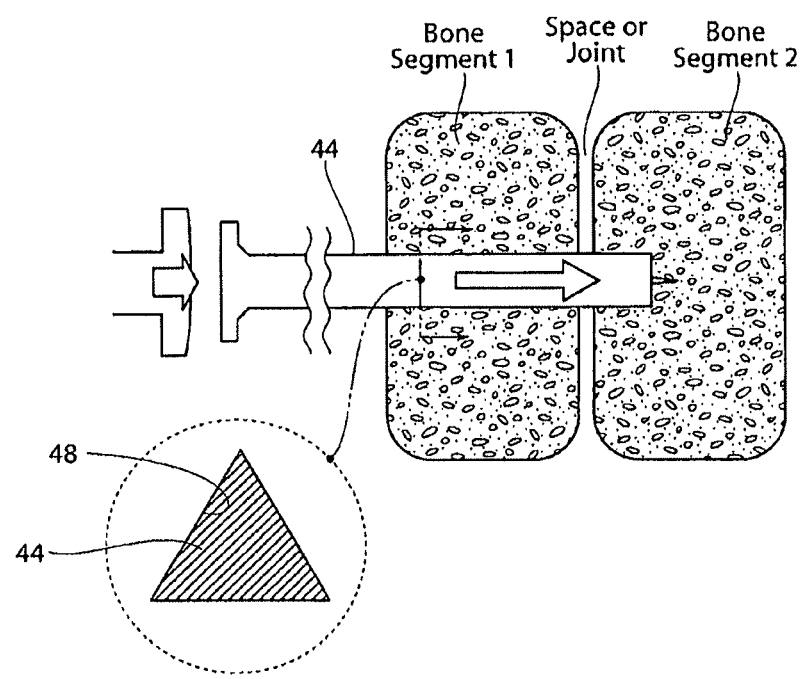

The shaped broach 44 is tapped into the pilot bore 42 over the guide pin 38 (and through the soft tissue protector) to create a broached bore 48 with the desired profile for the implant structure 20, which, in the illustrated embodiment, is triangular. This generally corresponds to the sequence shown diagrammatically in FIG. 2D. The triangular profile of the broached bore 48 is also shown in FIG. 5.

Figure 2E:
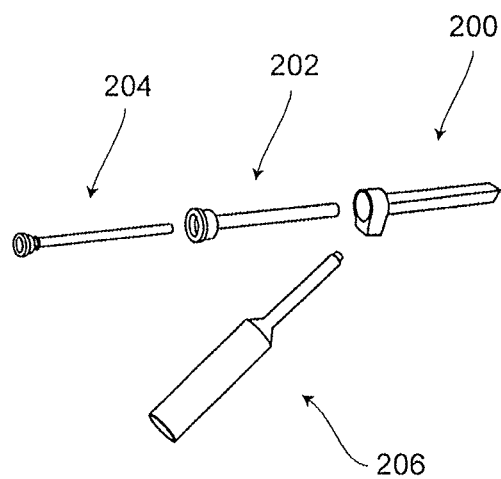
FIGS. 2E and 2F illustrate the assembly of a soft tissue protector system for placement over a guide wire.
Figure 2F:
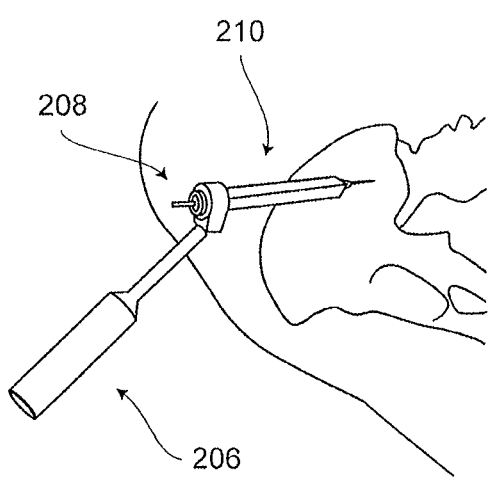

FIGS. 2E and 2F illustrate an embodiment of the assembly of a soft tissue protector or dilator or delivery sleeve 200 with a drill sleeve 202, a guide pin sleeve 204 and a handle 206. In some embodiments, the drill sleeve 202 and guide pin sleeve 204 can be inserted within the soft tissue protector 200 to form a soft tissue protector assembly 210 that can slide over the guide pin 208 until bony contact is achieved. The soft tissue protector 200 can be any one of the soft tissue protectors or dilators or delivery sleeves disclosed herein. In some embodiments, an expandable dilator or delivery sleeve 200 as disclosed herein can be used in place of a conventional soft tissue dilator. In the case of the expandable dilator, in some embodiments, the expandable dilator can be slid over the guide pin and then expanded before the drill sleeve 202 and/or guide pin sleeve 204 are inserted within the expandable dilator. In other embodiments, insertion of the drill sleeve 202 and/or guide pin sleeve 204 within the expandable dilator can be used to expand the expandable dilator.

In some embodiments, a dilator can be used to open a channel though the tissue prior to sliding the soft tissue protector assembly 210 over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

Figure 5:
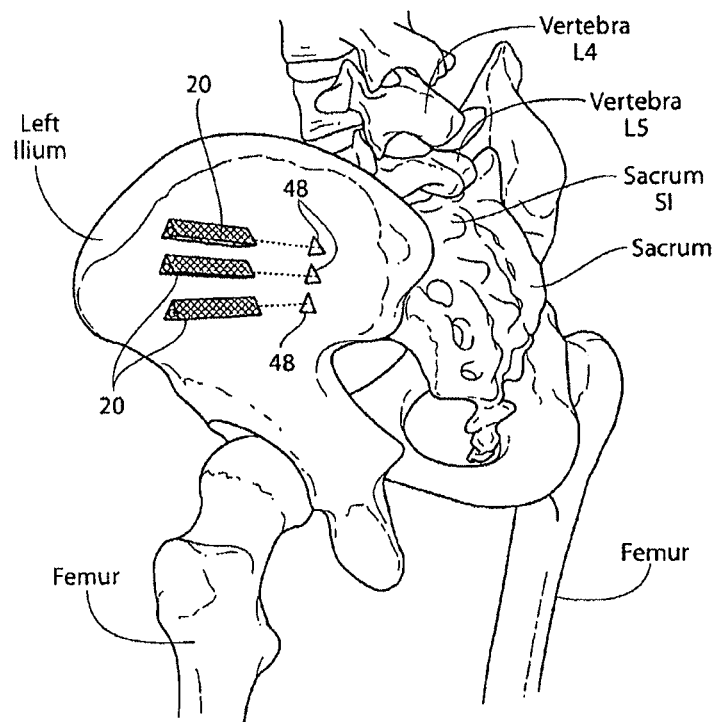
Figure 6:
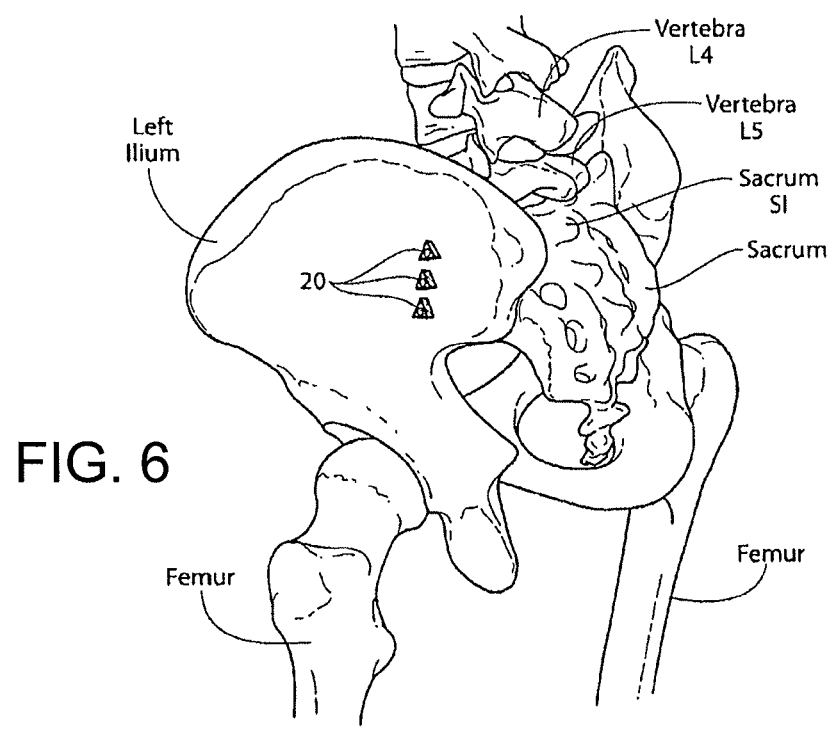
Figure 7A:
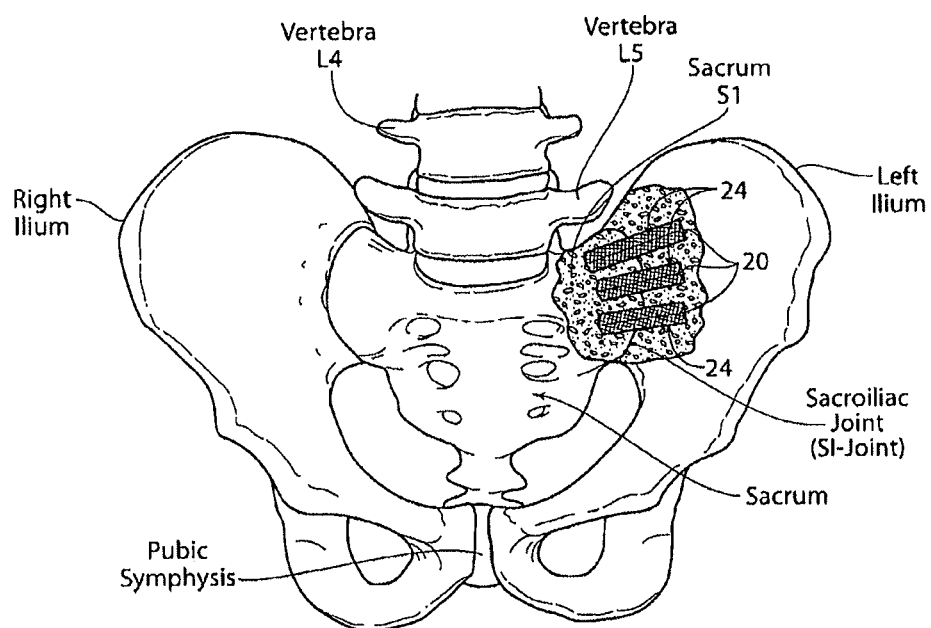
Figure 7B:
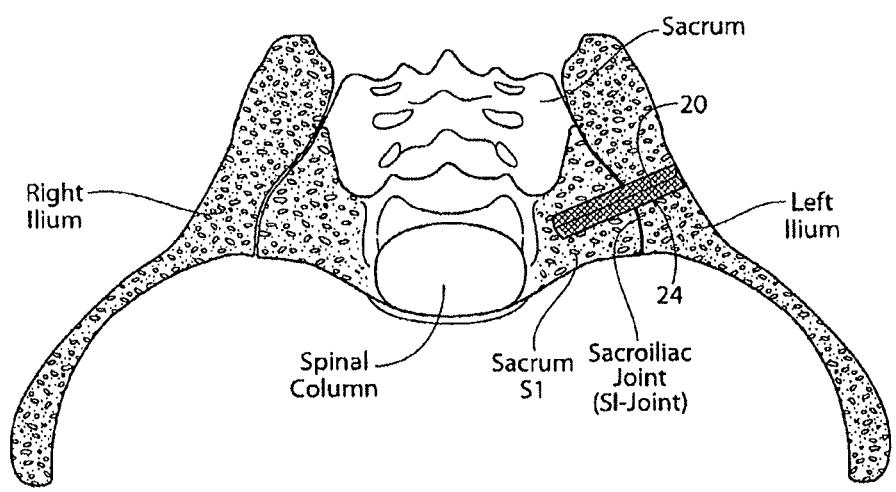

As shown in FIGS. 5 and 6, a triangular implant structure 20 can be now tapped through the soft tissue protector over the guide pin 38 through the ilium, across the SI-Joint, and into the sacrum, until the proximal end of the implant structure 20 is flush against the lateral wall of the ilium (see also FIGS. 7A and 7B). The guide pin 38 and soft tissue protector are withdrawn, leaving the implant structure 20 residing in the broached passageway, flush with the lateral wall of the ilium (see FIGS. 7A and 7B). In the illustrated embodiment, two additional implant structures 20 are implanted in this manner, as FIG. 6 best shows. In other embodiments, the proximal ends of the implant structures 20 are left proud of the lateral wall of the ilium, such that they extend 1, 2, 3 or 4 mm outside of the ilium. This ensures that the implants 20 engage the hard cortical portion of the ilium rather than just the softer cancellous portion, through which they might migrate if there was no structural support from hard cortical bone. The hard cortical bone can also bear the loads or forces typically exerted on the bone by the implant 20.

The implant structures 20 are sized according to the local anatomy. For the SI-Joint, representative implant structures 20 can range in size, depending upon the local anatomy, from about 35 mm to about 60 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone using, for example, plain film x-ray, fluoroscopic x-ray, or MRI or CT scanning.

Using a lateral approach, one or more implant structures 20 can be individually inserted in a minimally invasive fashion across the SI-Joint, as has been described. Conventional tissue access tools, obturators, cannulas, and/or drills can be used for this purpose. Alternatively, the novel tissue access tools described above and in U.S. Application No.

61/609,043, titled "TISSUE DILATOR AND PROTECTOR" and filed Mar. 9, 2012, which is hereby incorporated by reference in its entirety, can also be used. No joint preparation, removal of cartilage, or scraping are required before formation of the insertion path or insertion of the implant structures 20, so a minimally invasive insertion path sized approximately at or about the maximum outer diameter of the implant structures 20 can be formed.

The implant structures 20 can obviate the need for autologous bone graft material, additional pedicle screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20.

In a representative procedure, one to six, or perhaps up to eight, implant structures 20 can be used, depending on the size of the patient and the size of the implant structures 20. After installation, the patient would be advised to prevent or reduce loading of the SI-Joint while fusion occurs. This could be about a six to twelve week period or more, depending on the health of the patient and his or her adherence to post-op protocol.

The implant structures 20 make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 20 minimize or reduce rotation and micromotion. Rigid implant structures 20 made from titanium provide immediate post-op SI-Joint stability. A bony in-growth region 24 comprising a porous plasma spray coating with irregular surface supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded SI-Joint.

To improve the stability and weight bearing capacity of the implant, the implant can be inserted across three or more cortical walls. For example, after insertion the implant can traverse two cortical walls of the ilium and at least one cortical wall of the sacrum. The cortical bone is much denser and stronger than cancellous bone and can better withstand the large stresses found in the SI-Joint. By crossing three or more cortical walls, the implant can spread the load across more load bearing structures, thereby reducing the amount of load borne by each structure. In addition, movement of the implant within the bone after implantation is reduced by providing structural support in three locations around the implant versus two locations.

In some embodiments, the implant structure can function like a pedicle screw to allow fixation and/or fusion of bone such as the spine and/or SI-Joint. For example, long constructs can be used to join, fuse and/or stabilize a plurality of vertebrae in the thoracic, lumbar, and sacral portions of the spine. For example, to treat spinal disorders such as degenerative scoliosis, the L5 vertebra to the S1 vertebra can be fused using a system of implants and rods as described herein. As illustrated in FIGS. 8A-18E, the implant structure can include a stem portion and a head portion. The stem portion can be formed similarly to the SI-Joint implants described herein and in co-pending U.S. Patent Application Publication 2013/0296953, filed May 6, 2013, titled "Fenestrated Implant" and U.S. Pat. No. 8,202, 305 titled "Systems and Method for the Fixation or Fusion of Bone." A tulip or saddle structure can be attached to the head portion, and a rod can be inserted into and fixed to a plurality of tulip structures attached to implanted implant structures, thereby fusing and/or stabilizing the spine and/or other bones. In some embodiments, the stem portion, head portion, and tulip or saddle structure can all be cannulated and have a lumen that extends longitudinally through the assembled structure such that the assembled structure can be disposed over a guidewire or guide pin.

Figure 8C:
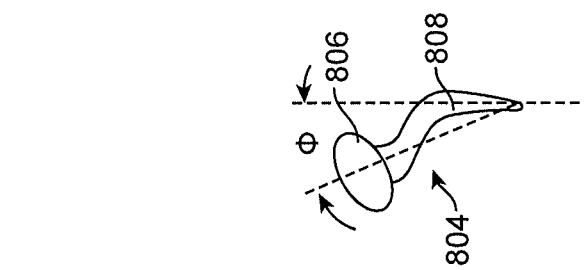
FIGS. 8A to 8C illustrate embodiments of an implant structure with a head portion joined using a Morse taper.
Figure 8B:
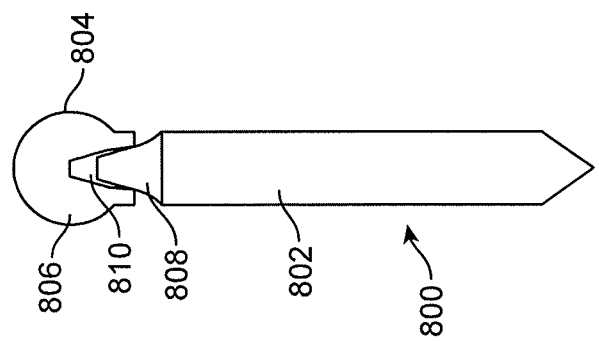
Figure 8A:
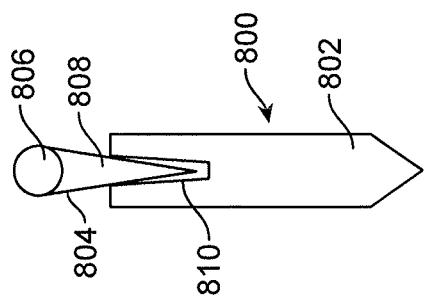

In some embodiments, as illustrated in FIGS. 8A-8C, the head portion 804 can be separate from the stem portion 802. For example, FIGS. 8A-8C illustrate embodiments of the implant structure 800 with a machine taper such as a Morse Taper. In some embodiments as illustrated in FIG. 8A, the head portion 804 can have a ball portion 806 and a tapered shank 808. The tapered shank 808 can fit into a corresponding tapering cavity 810 in the stem portion 802 to form a taper lock that is held together by friction. The length of the tapered shank 808 can be varied, making the distance between the ball portion 806 and proximal end of the stem portion 802 variable.

In some embodiments as illustrated in FIG. 8B, the head portion 804 can have a tapering cavity 810 while the stem portion 802 can have a tapered shank 808 extending from the proximal end of the stem portion 802. The length of the tapered shank 808 can be varied so that the distance between the head portion 804 and stem portion 802 can be adjusted as desired. In some embodiments, the tapered shank 808 of the stem portion 802 can be angled or curved with respect to the longitudinal axis of the stem portion 802. A curved tapered shank 808 can be useful as described below for the embodiment shown in FIG. 8C.

In some embodiments as illustrated in FIG. 8C, the head portion 804 can have a ball portion 806 and a tapered shank 808 that is curved or angled such that the distal portion of the tapered shank 808 is offset or angled with respect to the ball portion 806 and proximal portion of the tapered shank 808. A curved tapered shank 808 can be useful when a suitable implantation location in one or more bones is not aligned with the other implantation locations. In order for the implant structures 800 to line up with the stabilizing rod, a curved tapered shank 808 can be used so that the head portions 806 all line up with the stabilizing rod even if the implantation locations do not line up.

Figure 9:
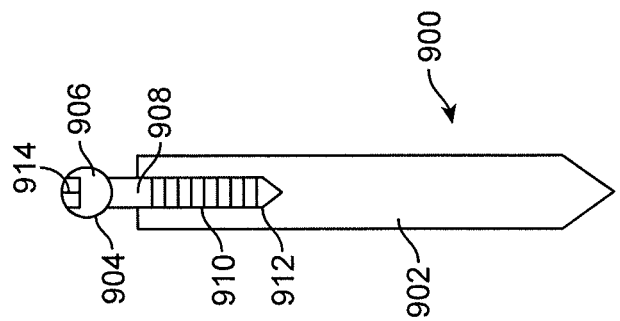
FIG. 9 illustrates an embodiment of an implant structure with a head portion joined using a screw type attachment.

FIG. 9 illustrates another embodiment of an implant structure 900 with a stem portion 902 and a head portion 904. The head portion 904 can have a ball portion 906 and a shank 908. The shank 908 can have threads 910, like a screw, that can be screwed into a cavity 912 with complementary internal threads. The ball portion 904 can have a screw drive 914 that facilitates turning of the head portion 904. The screw drive 914 can be a slot, socket (square, hex, star, etc.), or other typical screw drive 914 mechanism.

FIGS. 10A and 10B illustrate embodiments of integrated implant structures 1000 having a stem portion 1002 and a head portion 1004 that is integral with the stem portion 1002. As shown in FIGS. 10A and 10B, the head portion 1004 is integral or fixed to the stem portion 1002, and therefore the head portion 1004 has a fixed length relative to the stem portion 1002. As shown in FIG. 10A, the head portion 1004 can have a ball portion 1006 that can be attached to a tulip portion that is described in further detail below in, for example, FIGS. 13A and 18A-18C. Alternatively, as shown in FIG. 10B, the head portion 1004 can have a tulip portion 1007 integrated directly with the stem portion 1002. Having an integrated implant structure 1000 can be useful when it is known in advance that an implant structure 1000 will be used in, for example, a fixation or stabilization procedure that requires the use of an implant structure with a head portion 1004. The integrated implant 1000 can reduce procedure time by not requiring the attachment of the head portion 1004 onto the stem portion 1002. In addition, because the head portion 1004 is integral with the stem portion 1002, the integrated implant 1000 may have a greater structural integrity or strength than an implant assembled from separate pieces.

In some embodiments that may be particularly suited for pedicle screw salvage as illustrated in FIGS. 11A and 11B, the implant structure 1100 can have a stem portion 1102 with ledges or fenestrations 1003 that promote bone ingrowth. Examples of fenestrations that can be incorporated into the implant structure 1100 are described in co-pending U.S. Patent Application Publication 2013/0296953, filed May 6, 2013, titled "Fenestrated Implant." In some embodiments, the outer surface and/or structure of the stem portion 1102 can be twisted. In some embodiments, the stem portion 1102 may have a round cross-section to better match the cavity within the bone after the old pedicle screw has been removed. In some embodiments, the stem portion 1102 can be tapered. The diameter, shape and profile of the stem portion 1102 can match the bone cavity. In some embodiments, the stem portion 1102 can be oval, round, square, triangular, or rectilinear. In some embodiments, the head portion 1104 can be attached to the stem portion 1102 as described above. For example, the head portion 1104 can be attached to the stem portion 1102 using a Morse taper or screw attachment, or the head portion 1104 can be integral with the stem portion. Pedicle screw salvage can be performed when an implant, such as a pedicle screw, becomes loose within the bone due to windshield wipering or butterflying effects caused by stresses exerted to the bone by the implant. The loose implant can be removed and then replaced by one of the implants described herein.

Figure 12:
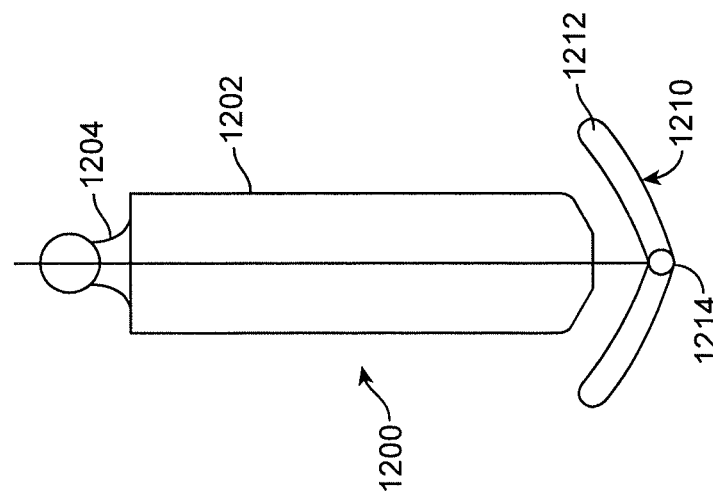
FIG. 12 illustrates an embodiment of an implant structure with an anchor.

FIG. 12 illustrates an implant structure 1200 with a stem portion 1202, a head portion 1204 attached to the proximal end of the stem portion 1202, and an anchor 1210 located distally the distal end of the stem portion 1202. The anchor 1210 can be folded into a collapsed configuration during insertion of the implant structure 1200 into bone, and then unfolded and/or expanded into an expanded configuration after insertion. In some embodiments, the anchor 1210 can have one or more arm portions 1212 that are foldable and/or expandable. In some embodiments, the anchor 1210 can be mechanically actuated from the collapsed configuration to the expanded configuration. In some embodiments, the arm portions 1212 can be joined at a hinge or a hub 1214. In some embodiments, the arm portions 12 can be expanded like the frame of an umbrella. In other embodiments, the anchor 1210 can be self-expanding and can be made of a shape memory material such as a nickel titanium alloy. In some embodiments, the anchor 1210 can be restrained by a sheath or other restraining element when in the collapsed configuration. In some embodiments, the anchor 1210 can be attached to and/or extend from the distal end of the stem portion 1202. The anchor 1210 can reduce or prevent implant structure 1200 migration after implantation.

Figure 13B:
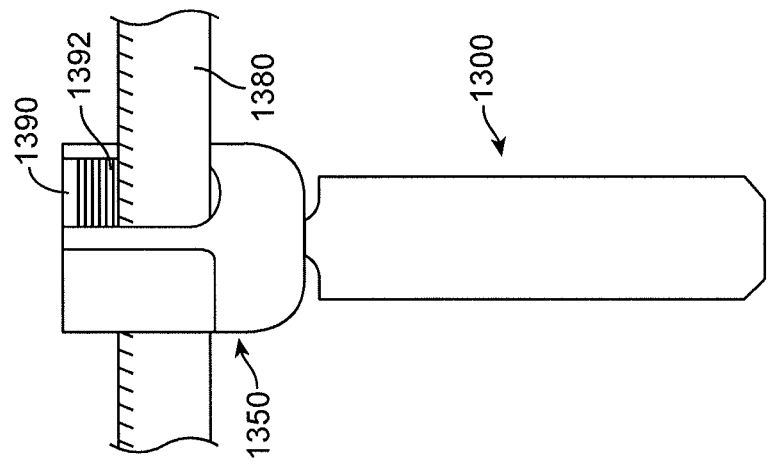
FIGS. 13A and 13B illustrate the attachment of a tulip structure to an implant structure and the securing of a rod to the tulip structure.
Figure 13A:
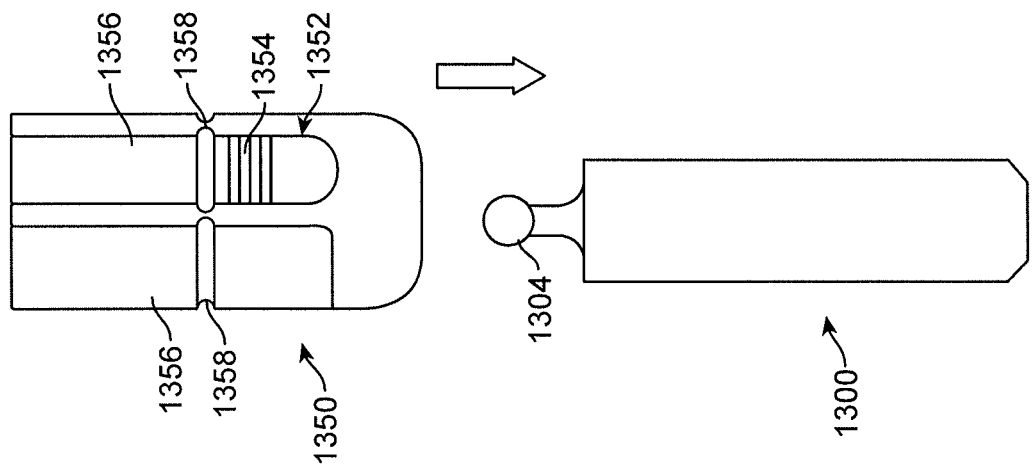

FIGS. 13A and 13B illustrate an implant structure 1300 and a corresponding tulip or saddle structure 1350 that can be attached to the head portion 1304 of the implant structure 1300. The tulip structure 1350 can have a slot 1352 for receiving a rod 1380 that can be used to stabilize the spine. In some embodiments, the tulip structure 1350 can have internal threading 1354 on the two wall portions 1356 that form the slot 1352. In some embodiments, a locking screw 1390 can be used to lock and secure the rod 1380 in place within the tulip structure 1350. The locking screw 1390 can have threading 1392 that correspond to the internal threading 1354 on the two wall portions 1356. To lock and secure the rod in place, the locking screw can simply be screwed in place over the rod 1380. The locking screw 1390 can have a screw drive similar to screw drive 914 described above with respect to FIG. 9. In other embodiments, other fastening mechanisms can be used in place of the locking screw 1390 to hold the rod in place. In some embodiments, the top portions of the wall portions 1356 can be snapped off along a break line 1358. In some embodiments, the break line 1358 can be formed by scoring or thinning the wall portions 1356 along the break line 1358. In some embodiments, the tulip structure 1350 does not have any break lines 1358 or excess wall portions 1356 that can be broken off and can instead have wall portions 1356 that are sized to receive the rod 1380 and locking screw 1390 without having excess material extending past the locking screw 1390.

FIG. 14 illustrates another embodiment of an implant structure 1400 having a stem portion 1402 with a cavity 1412 for receiving an expandable attachment 1410 on the shank 1408 of the head portion 1404. The expandable attachment 1410 on the shank 1408 can have a collapsed configuration and an expanded configuration. The entrance to the cavity 1412 can be a narrowed opening 1414 with a diameter less than the diameter of the cavity 1412. The shank 1408 can be inserted through the narrowed opening 1414 and into the cavity 1412 with the expandable attachment 1410 in the collapsed configuration. Once in the cavity 1412, the expandable attachment 1410 can expand into the expanded configuration, thereby securing the head portion 1404 to the stem portion 1402. The head portion 1404 can have a ball portion 1406 for connected to a tulip structure.

FIG. 15 illustrates another embodiment of a head portion 1504 that can be secured into a cavity 1412 in a stem portion 1402 similar to that illustrated in FIG. 14. The head portion 1504 can have a ball portion 1506 and a shank 1508 with narrowed or undercut portion 1508 and a tapered distal portion 1510. The tapered distal portion 1510 has an end that is narrow enough to be inserted into the narrowed opening 1414. As the tapered distal portion 1510 is further inserted through the narrowed opening 1414, the tapered distal portion 1510 forces the narrowed opening to open wider until the narrowed opening snaps into the undercut portion 1508 of the shank 1508, which in combination with the tapered distal portion 1510 in the cavity, functions to secure the head portion 1504 to the stem portion 1402.

FIG. 16 illustrates another embodiment of a head portion 1604 than can be screwed into an implant structure 1600 in a similar manner as described in connection with FIG. 9, except that in this embodiment, the shank 1608 can have a length that allows the shank 1608 to extend completely through the implant structure 1600. Similarly to the embodiment described in FIG. 9, the shank 1608 can be threaded 1610 and a screw drive on the head portion 1604 can be used to turn the screw like shank 1608. In some embodiments, the threads 1610 on the proximal portion of the shank 1608 can be machine threads for engaging the corresponding threads in the implant structure 1600. The threads 1610 on the distal portion of the shank 1608 can be deeper than the machine threads, which allow the threads to better engage cancellous bone. In some embodiments, the pitch of the threads 1610 can be constant along the length of the shank 1608. In other embodiments, the pitch of the threads 1610 can vary between the different thread types.

FIG. 17 illustrates another embodiment of the attachment of the stem portion 1702 of an implant structure 1700 to a head portion 1704. In this embodiment, the stem portion 1702 has a socket 1708 for receiving a corresponding ball 1706 on the distal end of the head portion 1704. The ball 1706 can reside in the socket 1708 to form a ball and socket joint that permits the head portion 1704 to be rotated through a predetermined angle of rotation. In some embodiments, the angle of rotation can be about 60 degrees or less. In other embodiments, the angle of rotation can be between about 30 to 90 degrees or less.

FIGS. 18A-18E illustrate embodiments of a snap-on tulip or saddle structure 1850. In some embodiments, the tulip structure 1850 can have a slot 1852 for receiving a rod that can be used to stabilize the spine or other bones. In some embodiments, the tulip structure 1850 can have internal threading on the two wall portions 1856 that form the slot 1852. In some embodiments, the wall portions 1856 can have extended tabs that can be snapped off and removed. In some embodiments, the tulip structure 1850 can have a head portion receiving slot 1858 shaped to receive the head portion 1804 attached to the implant structure 1800. The head portion receiving slot 1858 can be located on the distal end of the tulip structure 1850 and provides access to the internal cavity of the tulip structure 1850. The distal end of the tulip structure can have an opening 1860 that allows a portion of the implant structure 1800 to extend through. The diameter or size of the opening 1860 is less than the diameter or size of the head portion 1804, which allows the tulip structure 1850 to receive and then retain the head portion within the cavity of the tulip structure 1850. A stabilizing rod can then be fixed in place within the slot 1852 of the tulip structure 1850, thereby securing the head portion 1804 to the tulip structure 1850.

In some embodiments, the head portion receiving slot 1858 runs up both a portion of one of the side walls and the along the bottom portion to the opening 1860. In some embodiments, the upper portion of the head portion receiving slot 1858 can be circular in shape to accommodate the ball portion of the head portion 1804. The circular portion of the head portion receiving slot 1858 can be located a sufficient distance from the bottom portion of the tulip structure 1850 such that after the ball portion of the head portion 1804 passes into the cavity of the tulip structure 1850, the ball portion drops down against the bottom portion which prevents the ball portion from inadvertently sliding out of the tulip structure 1850. In order for the ball portion of the head portion 1804 to be removed from the tulip structure 1850, the ball portion must be raised from the bottom of the tulip structure 1850 until the ball portion is aligned with the circular portion of the head portion receiving slot 1858, and then the head portion 1804 can be removed from the tulip structure. In some embodiments, the portion of the head portion receiving slot 1858 on the bottom part of the tulip structure can be a straight slot. In other embodiments, the portion of the head portion receiving slot 1858 on the bottom part of the tulip structure can be a curved slot.

The shape and structure of the tulip structure 1850 cavity and opening 1860 allows the tulip structure 1850 to have about a 60 degree angle of movement and rotation after being attached to the head portion 1804. Such a tulip structure 1850 and head portion 1804 can be referred to as poly-axial, meaning the tulip structure 1850 can freely move within a conical area. In other embodiments, the angle of movement and rotation can be between about 30 to 90 degrees or less. Having a substantial angle of movement and rotation allows the implant structure 1800 to be inserted in a wider variety of angles while still allowing the tulip structure 1850 to be aligned with the rod for fixation.

Any of the implants described herein can be used in a variety of surgical procedures, such as stabilization, fixation or fusion of the sacroiliac joint and/or the spine, including vertebra and facet joints. In addition, surgical procedures using a posterior or a posterolateral approach will be particularly suitable for use with the implant structures described herein since the tulip structure of the implant will be aligned with the other implants along the spine after implantation. As described herein, these implant structures can be connected together using a rod that can be secured to each tulip structure. For simplicity, the following procedures will be illustrated and described using a general implant structure 20, but it is understood that any of the implant structures described herein can be used in place of the general implant structure 20.

Figure 19A:
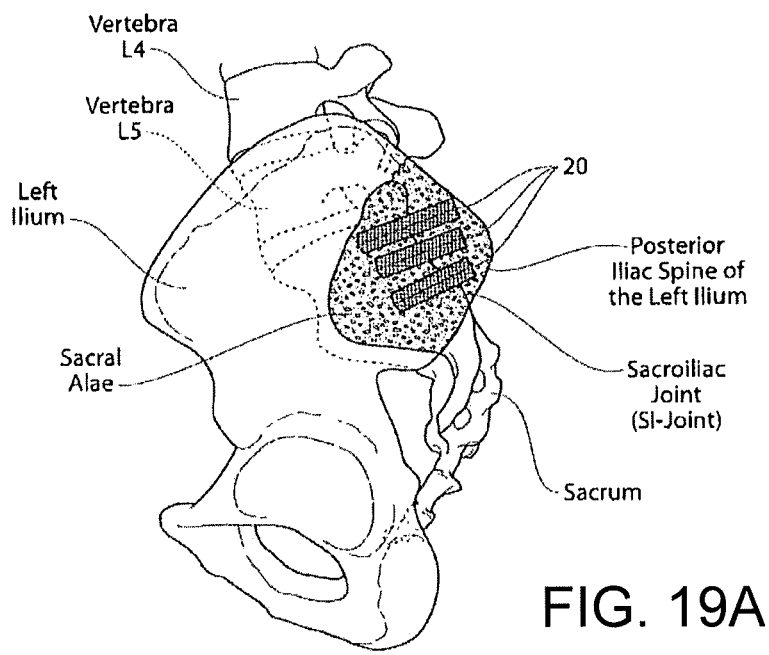
FIGS. 19A and 19B illustrate a lateral view and an axial view of an embodiment of the implant structure crossing the SI-Joint using a posterolateral approach entering from the posterior iliac spine of the ilium, angling through the SI-Joint, and terminating in the sacral alae.
Figure 19B:
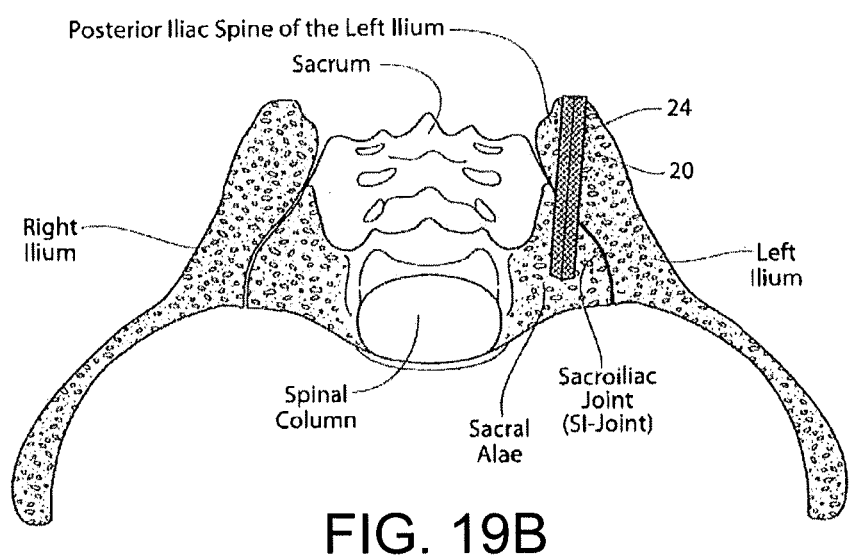

For example, FIGS. 19A and 19B illustrate a lateral view and an axial view of an embodiment of the implant structure crossing the SI-Joint using a posterolateral approach entering from the posterior iliac spine of the ilium, angling through the SI-Joint, and terminating in the sacral alae.

The posterolateral approach involves less soft tissue disruption that the lateral approach, because there is less soft tissue overlying the entry point of the posterior iliac spine of the ilium. Introduction of the implant structure 20 from this region therefore makes possible a smaller, more mobile incision. Further, the implant structure 20 passes through more bone along the posterolateral route than in a strictly lateral route, thereby involving more surface area of the SI-Joint and resulting in more fusion and better fixation of the SI-Joint. Employing the posterolateral approach also makes it possible to bypass all nerve roots, including the L5 nerve root.

The set-up for a posterolateral approach is generally the same as for a lateral approach. It desirably involves the identification of the SI-Joint segments that are to be fixated or fused (arthrodesed) using, e.g., the Faber Test, or CT-guided injection, or X-ray/MRI of SI-Joint. It is desirable performed with the patient lying in a prone position (on their stomach) and is aided by lateral and anterior-posterior (A-P) c-arms. The same surgical tools are used to form the pilot bore 42 over a guide pin 38, except the path of the pilot bore 42 now starts from the posterior iliac spine of the ilium, angles through the SI-Joint, and terminates in the sacral alae. The pilot bore 42 is shaped into the desired profile using a broach, as before described, and the implant structure 20 is inserted into the broached bore 48. The implant structure 20 is tapped through the soft tissue protector over the guide pin 38 from the posterior iliac spine of the ilium, angling through the SI-Joint, and terminating in the sacral alae, until the proximal end of the implant structure 20 is flush against the posterior iliac spine of the ilium. Because of the anatomic morphology of the bone along the posterolateral route, it may be advisable to introduce implant structures of difference sizes, with the most superior being the longest in length, and the others being smaller in length.

Figure 20A:
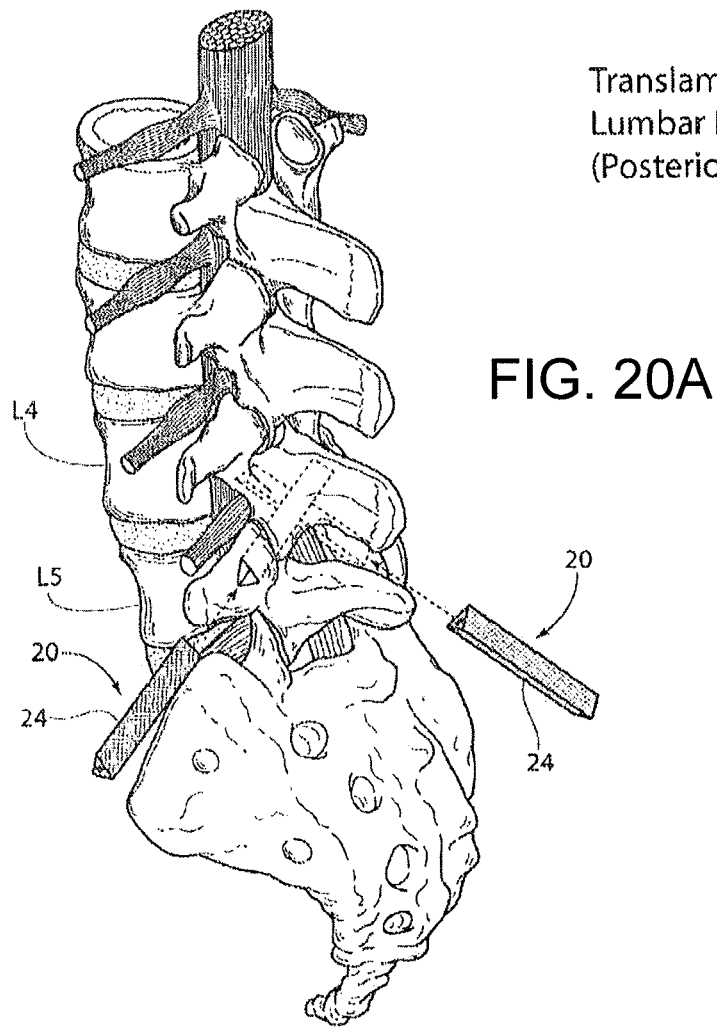
FIG. 20A is an anatomic posterior perspective view, exploded prior to implantation, of a representative configuration of an assembly of one or more implant structures, sized and configured to achieve translaminar lumbar fusion in a non-invasive manner and without removal of the intervertebral disc.
Figure 20B:
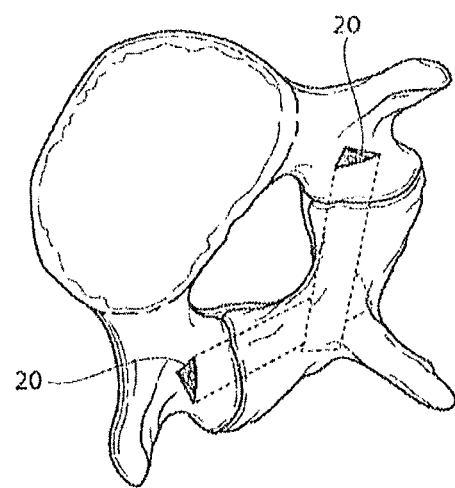
FIG. 20B is an anatomic inferior transverse plane view showing the assembly shown in FIG. 20A after implantation.

FIG. 20A shows, in an exploded view prior to implantation, a representative configuration of an assembly of one or more implant structures 20 sized and configured to achieve translaminar lumbar fusion in a non-invasive manner and without removal of the intervertebral disc. FIG. 20B shows the assembly after implantation, respectively, in an inferior transverse plane view.

As can be seen in the representative embodiment illustrated in FIGS. 20A and 20B, the assembly comprises two implant structures 20. The first implant structure 20 extends from the left superior articular process of vertebra L5, through the adjoining facet capsule into the left inferior articular process of vertebra L4, and, from there, further through the lamina of vertebra L4 into an interior right posterolateral region of vertebra L4 adjacent the spinous process. The second implant structure 20 extends from the right superior articular process of vertebra L5, through the adjoining facet capsule into the right inferior articular process of vertebra L4, and, from there, further through the lamina of vertebra L4 into an interior left posterolateral region of vertebra L4 adjacent the spinous process. The first and second implant structures 20 cross each other within the medial lamina of vertebra L4.

The first and second implant structures 20 are sized and configured according to the local anatomy. The selection of a translaminar lumbar fusion (posterior approach) is indicated when the facet joints are aligned with the sagittal plane. Removal of the intervertebral disc is not required, unless the condition of the disc warrants its removal.

A posterior procedure for implanting the assembly of implant structures 20 shown in FIGS. 20A and 20B comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to establish a desired implantation path through bone for the first (e.g., left side) implant structure 20, which, in FIGS. 20A and 20B, traverses through the left superior articular process of vertebra L5, through the adjoining facet capsule into the left inferior articular process of vertebra L4, and then through the lamina of vertebra L4 into an interior right posterolateral region of vertebra L4 adjacent the spinous process. The method further includes (iv) guided by the guide pin, increasing the cross section of the path; (v) guided by the guide pin, shaping the cross section of the path to correspond with the cross section of the implant structure; (vi) inserting the implant structure 20 through the path over the guide pin; (vii) withdrawing the guide pin; and (viii) using a guide pin to established a desired implantation path through bone for the second (e.g., right side) implant structure 20, which, in FIGS. 20A and 20B, traverses through the right superior articular process of vertebra L5, through the adjoining facet capsule into the right inferior articular process of vertebra L4, and through the lamina of vertebra L4 into an interior left posterolateral region of vertebra L4 adjacent the spinous process. The physician repeats the remainder of the above-described procedure sequentially for the right implant structure 20 as for the left, and, after withdrawing the guide pin, closes the incision.

The intimate contact created between the bony in-growth or through-growth region 24 along the surface of the implant structure 20 across the facet joint accelerates bony in-growth or through-growth onto, into, or through the implant structure 20, to accelerate fusion of the facets joints between L4 and L5. Of course, translaminar lumbar fusion between L5 and S1 can be achieved using first and second implant structures in the same manner.

Figure 21A:
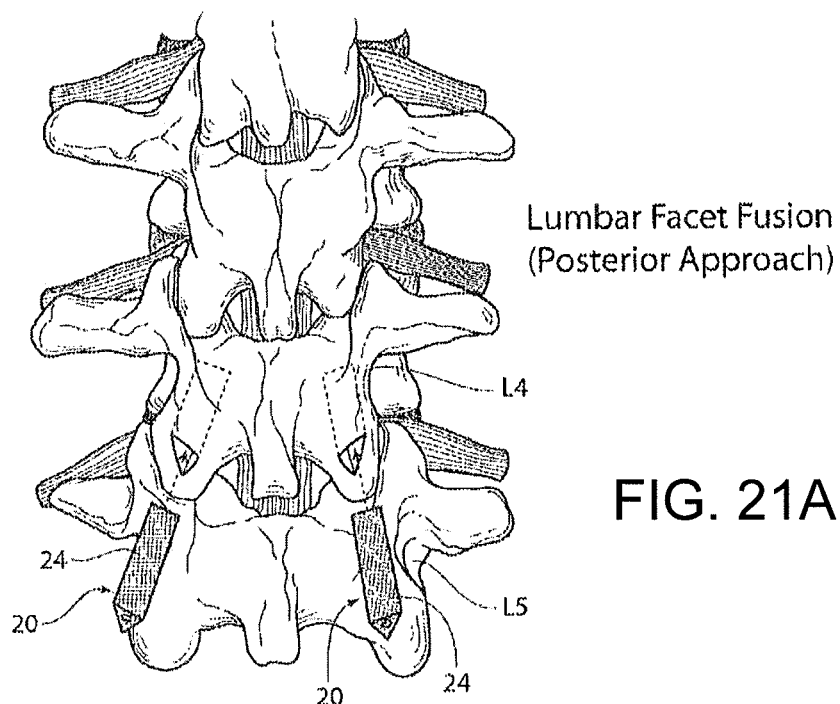
FIG. 21A is an anatomic posterior perspective view, exploded prior to implantation, of a representative configuration of an assembly of one or more implant structures, sized and configured to achieve lumbar facet fusion, in a non-invasive manner.
Figure 21B:
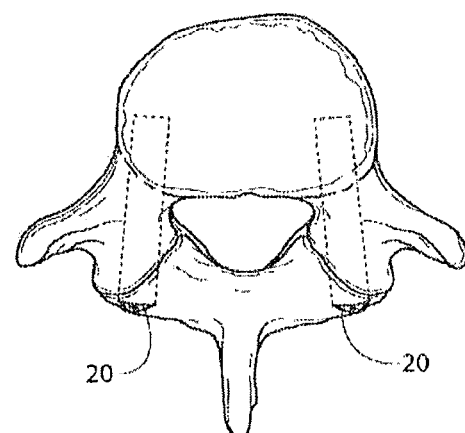
FIG. 21B is an anatomic inferior transverse plane view showing the assembly shown in FIG. 21A after implantation.
Figure 21C:
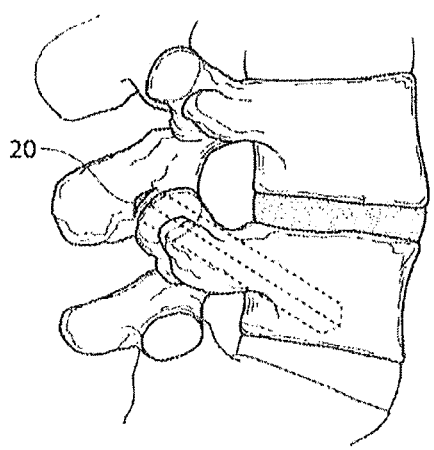
FIG. 21C is an anatomic lateral view showing the assembly shown in FIG. 21A after implantation.

FIG. 21A shows, in an exploded view prior to implantation, a representative configuration of an assembly of one or more implant structures 20 sized and configured to lumbar facet fusion, in a non-invasive manner and without removal of the intervertebral disc. FIGS. 21B and 21C show the assembly after implantation, respectively, in an inferior transverse plane view and a lateral view.

As can be seen in the representative embodiment illustrated in FIGS. 21A to 21C, the assembly comprises two implant structures 20. The first implant structure 20 extends from the left inferior articular process of vertebra L4, through the adjoining facet capsule into the left superior articular process of vertebra L5 and into the pedicle of vertebra L5. The second implant structure 20 extends from the right inferior articular process of vertebra L5, through the adjoining facet capsule into the right superior articular process of vertebra L5 and into the pedicle of vertebra L5. In this arrangement, the first and second implant structures 20 extend in parallel directions on the left and right pedicles of vertebra L5. The first and second implant structures 20 are sized and configured according to the local anatomy. The selection of lumbar facet fusion (posterior approach) is indicated when the facet joints are coronally angled. Removal of the intervertebral disc is not necessary, unless the condition of the disc warrants its removal.

A posterior procedure for implanting the assembly of implant structures 20 shown in FIGS. 21A to 21C comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20, which, in FIGS. 21A to 21C, traverses through the left inferior articular process of vertebra L4, through the adjoining facet capsule into the left superior articular process of vertebra L5 and into the pedicle of vertebra L5. The method further includes (iv) guided by the guide pin, increasing the cross section of the path; (v) guided by the guide pin, shaping the cross section of the path to correspond with the cross section of the implant structure 20; (vi) inserting the implant structure 20 through the path over the guide pin; (vii) withdrawing the guide pin; and (viii) using a guide pin to establish a desired implantation path through bone for the second (e.g., right side) implant structure 20, which, in FIGS. 21A to 21C, traverses through the right inferior articular process of vertebra L4, through the adjoining facet capsule into the right superior articular process of vertebra L5 and into the pedicle of vertebra L5. The physician repeats the remainder of the above-described procedure sequentially for the right implant structure 20 as for the left and, withdrawing the guide pin, closes the incision.

The intimate contact created between the bony in-growth or through-growth region 24 along the surface of the implant structure 20 across the facet joint accelerates bony in-growth or through-growth onto, into, or through the implant structure 20, to accelerate fusion of the facets joints between L4 and L5.

Of course, transfacet lumbar fusion between L5 and S1 can be achieved using first and second implant structures in the same manner.

Figure 22A:
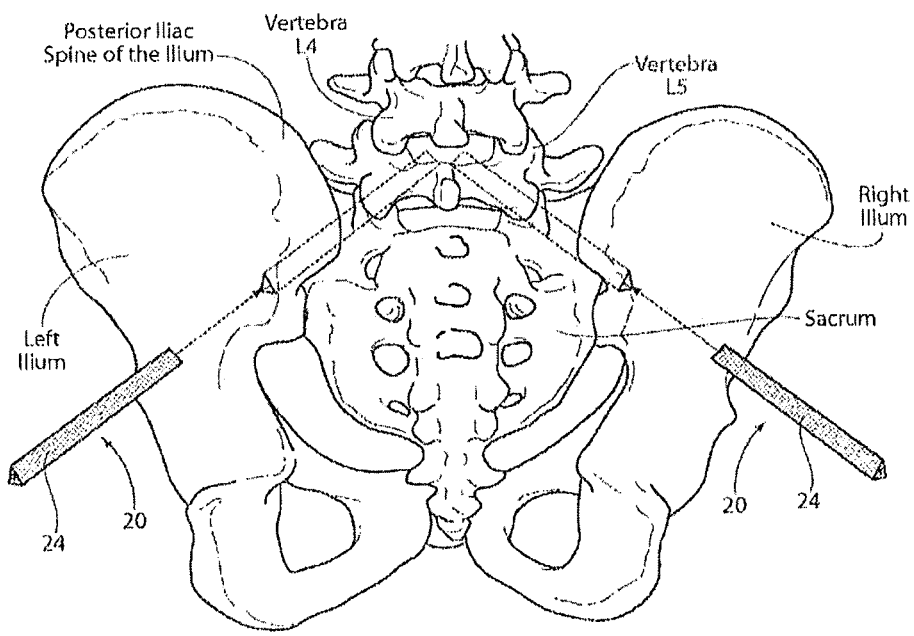
FIG. 22A is an anatomic posterior view showing, in an exploded view prior to implantation, another representative configuration of an assembly of one or more implant structures sized and configured to achieve fusion between lumbar vertebra L5 and sacral vertebra S1, in a non-invasive manner and without removal of the intervertebral disc, using a posterolateral approach entering from the posterior iliac spine of the ilium, angling through the SI-Joint, and terminating in the lumbar vertebra L5.
Figure 22B:
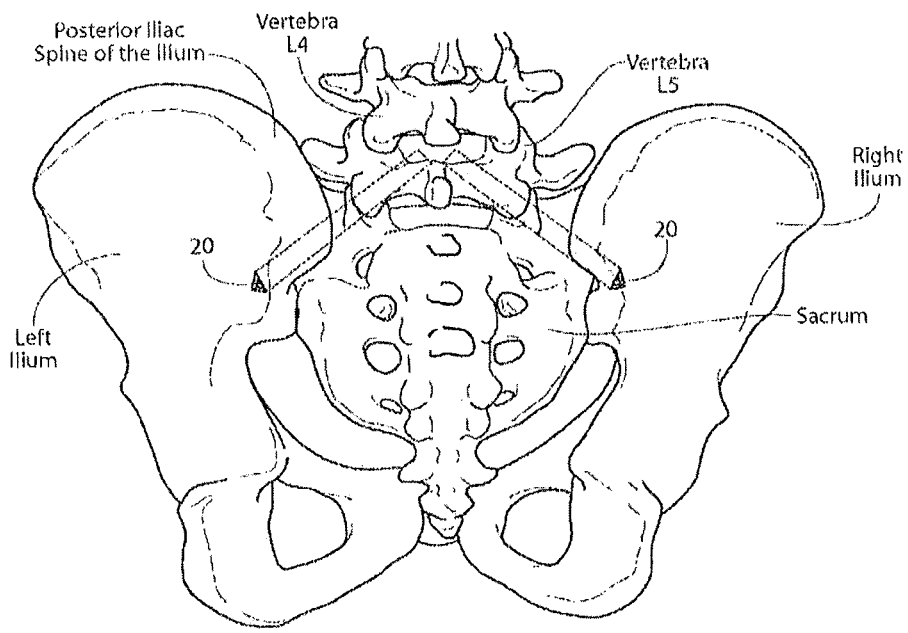
FIG. 22B is an anatomic posterior view showing the assembly shown in FIG. 22A after implantation.

FIG. 22A shows, in an exploded view prior to implantation, another representative configuration of an assembly of one or more implant structures 20 sized and configured to achieve fusion between lumbar vertebra L5 and sacral vertebra S1, in a non-invasive manner and without removal of the intervertebral disc. FIGS. 22B and 22C show the assembly after implantation.

As FIGS. 22A and 22B show, the one or more implant structures are introduced in a posterolateral approach entering from the posterior iliac spine of the ilium, angling through the SI-Joint into and through the sacral vertebra S1, and terminating in the lumbar vertebra L5. This path and resulting placement of the implant structures 20 are also shown in FIG. 22C. In the illustrated embodiment, two implant structures 20 are placed in this manner, but there can be more or fewer implant structures 20. Also in the illustrated embodiment, the implant structures 20 are triangular in cross section, but it should be appreciated that implant structures 20 of other cross sections as previously described can be used.

The posterolateral approach involves less soft tissue disruption than the lateral approach, because there is less soft tissue overlying the entry point of the posterior iliac spine of the ilium. Introduction of the implant structure 20 from this region therefore makes possible a smaller, more mobile incision.

The set-up for a posterolateral approach is generally the same as for a lateral approach. It desirably involves the identification of the lumbar region that is to be fixated or fused (arthrodesed) using, e.g., the Faber Test, or CT-guided injection, or X-ray/MRI of the L5-S1 level. It is desirable performed with the patient lying in a prone position (on their stomach) and is aided by lateral and anterior-posterior (A-P) c-arms. The same surgical tools are used to form the pilot bore over a guide pin (e.g., on the right side), except the path of the pilot bore now starts from the posterior iliac spine of the ilium, angles through the SI-Joint, and terminates in the lumbar vertebra L5. The broached bore is formed, and the right implant 20 structure is inserted. The guide pin is withdrawn, and the procedure is repeated for the left implant structure 20, or vice versa. The incision site(s) are closed.

The assembly as described makes possible the achievement of trans-iliac lumbar fusion using a posterolateral approach in a non-invasive manner, with minimal incision, and without necessarily removing the intervertebral disc between L5 and S1.

Figure 23A:
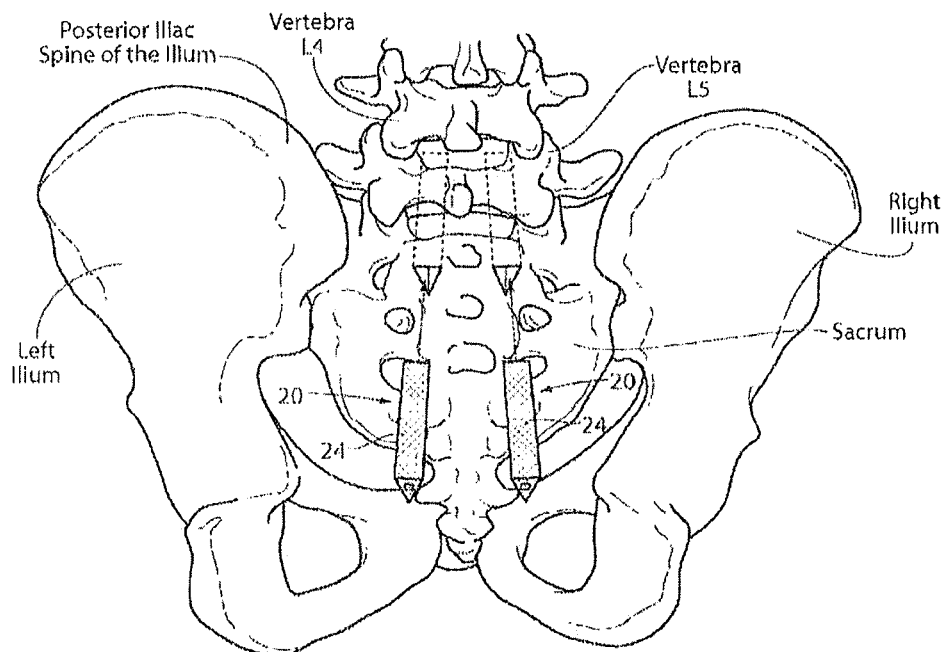
FIG. 23A is an anatomic anterior perspective view showing, in an exploded view prior to implantation, a representative configuration of an assembly of one or more implant structures, sized and configured to stabilize a spondylolisthesis at the L5/S1 articulation.
Figure 23B:
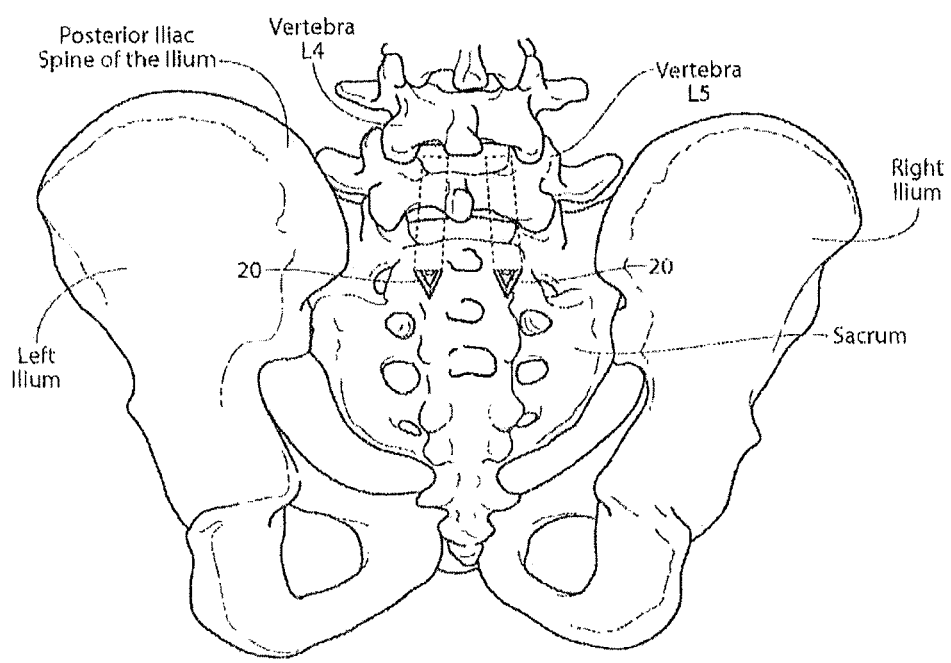
FIG. 23B is an anatomic anterior perspective view showing the assembly shown in FIG. 23A after implantation.
Figure 23C:
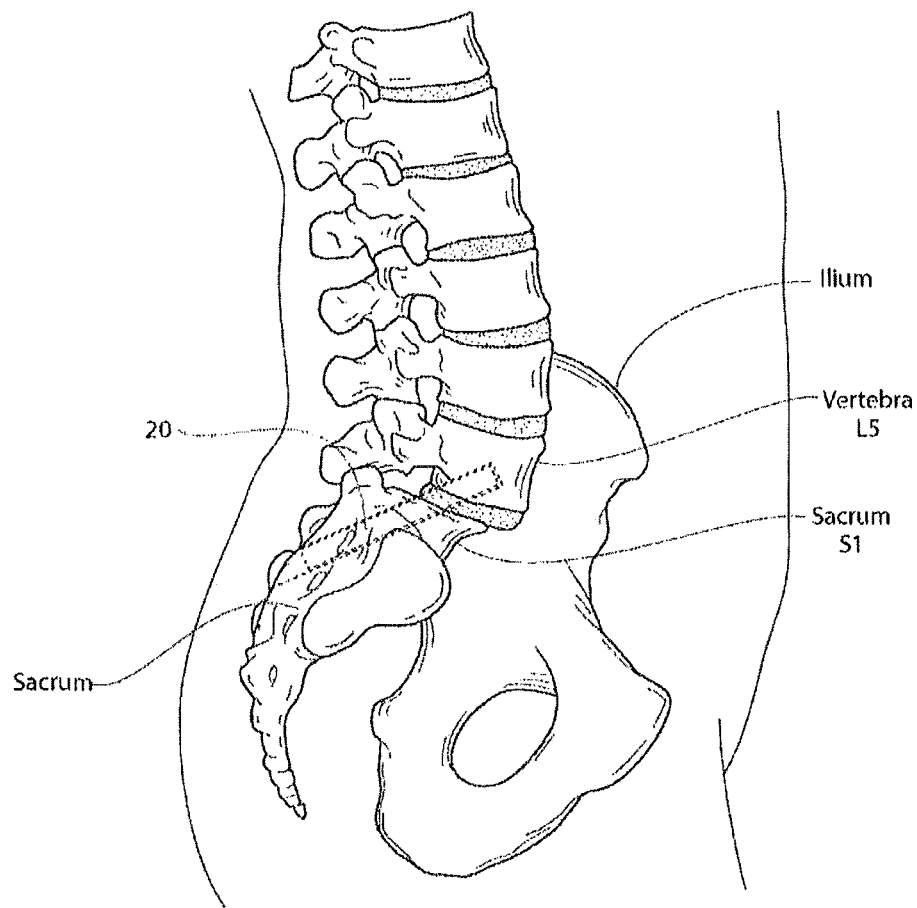
FIG. 23C is an anatomic lateral view showing the assembly shown in FIG. 23B.

FIG. 23A shows, in an exploded view prior to implantation, a representative configuration of an assembly of one or more implant structures 20 sized and configured to stabilize the spondylolisthesis at the L5/S1 articulation. FIGS. 23B and 23C show the assembly after implantation.

As shown, the implant structure 20 extends from a posterolateral region of the sacral vertebra S1, across the intervertebral disc into an opposite anterolateral region of the lumbar vertebra L5. The implant structure 20 extends in an angled path (e.g., about 20 degrees to about 40 degrees off horizontal) through the sacral vertebra S1 in a superior direction, through the adjoining intervertebral disc, and terminates in the lumbar vertebra L5.

A physician can employ a posterior approach for implanting the implant structure 20 shown in FIGS. 23A, 23B, and 23C, which includes forming a pilot bore over a guide pin inserted in the angled path from the posterior of the sacral vertebra S1 through the intervertebral disc and into an opposite anterolateral region of the lumbar vertebra L5, forming a broached bore, inserting the implant structure 20, and withdrawing the guide pin. The incision site is then closed. As previously described, more than one implant structure 20 can be placed in the same manner to stabilize a spondylolisthesis.

The physician can, if desired, combine stabilization of the spondylolisthesis, as shown in FIG. 23A/B/C, with a reduction, realigning L5 and S-1. The physician can also, if desired, combine stabilization of the spondylolisthesis, as shown in FIG. 23A/B/C (with or without reduction of the spondylolisthesis), with a lumbar facet fusion, as shown in FIGS. 21A to 21C. The physician can also, if desired, combine stabilization of the spondylolisthesis, as shown in FIG. 23A/B/C, with a decompression, e.g., by the posterior removal of the spinous process and laminae bilaterally.

Figure 24:
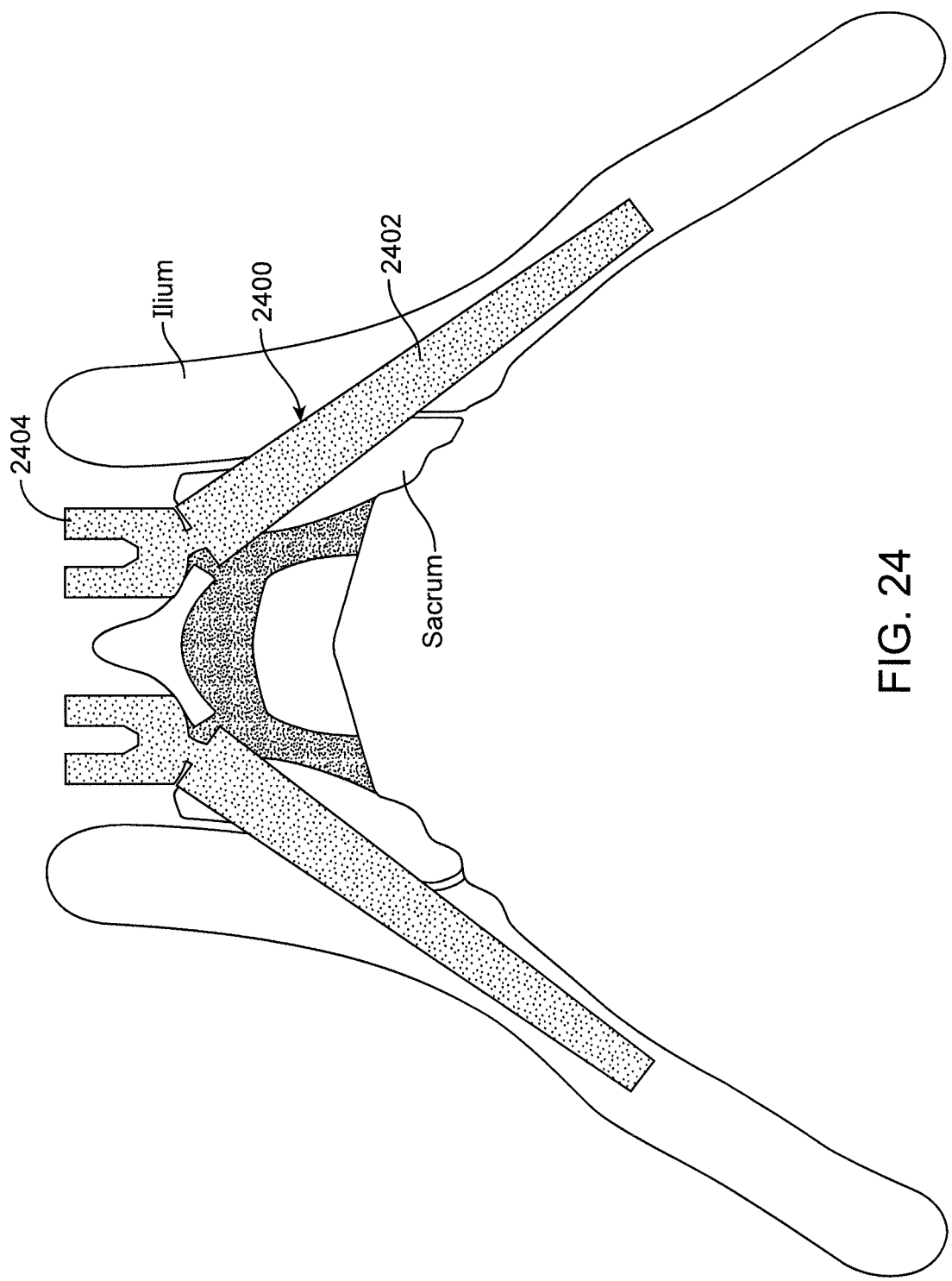
FIG. 24 is an axial view illustrating an implant inserted through a posteromedial approach.

In addition, in some embodiments as shown in FIG. 24, a posteromedial approach can be used to insert the implant 2400. For example, the implant 2400 can be inserted through the posterolateral sacrum, across the alae, through the SI-joint, and into the ilium where the implant may terminate. As illustrated, the implant 2400 can have a stem portion 2402 that is inserted into the bone and a tulip portion 2404 that remains outside the bone. In some implementations, a particular posteromedial approach may be used which is known as an S2 alar-iliac (S2AI) approach. The entry point for the S2AI approach is located at the midpoint between the S1 and S2 foramen and 2 mm medial to the lateral sacral crest. The guidewire and or implant should be placed across the sacro-iliac joint above the superior rim of the sciatic notch.

In some implementations, just one implant is placed across each SI-joint using an S2AI trajectory, as depicted in FIG. 24. In other implementations, an implant can be added above and or below each S2AI implant using a lateral approach through the ilium, the SI-Joint, and into the sacrum, such as depicted in FIGS. 6A-7B.

It should be noted that, according to aspects of the present disclosure, a tulip, saddle structure, poly-axial joint, fastening mechanism or other coupling device (such as shown in FIGS. 13A and 13B) can be coupled to the proximal end of any number of bone anchors. For example, a coupling device may be attached to the proximal end of any of the implants previously shown in this disclosure, such as those shown in FIGS. 1 and 8A-18E, to allow the implant to couple with a spinal rod or construct, such as rod 1380 shown in FIG. 13B. In a similar manner, a coupling device may be located on the proximal end of the implant shown in FIGS. 1-2 or the implant shown in FIGS. 31-34 of U.S. Pat. No. 8,734,462. In some embodiments, a coupling device may be attached to the proximal end of any of the implants shown in FIGS. 1B-2B, 9A-9B and 10A-10B of U.S. Patent Application Publication 2013/0245763. In some embodiments, a coupling device may be attached to the proximal end of any of the implants shown in FIGS. 47-49 of U.S. Patent Application Publication 2017/0007409. In some embodiments, a coupling device may be attached to the proximal end of the implant shown in FIG. 12 of U.S. Pat. No. 9,662,157. In some embodiments, a coupling device may be attached to the proximal end of any of the implants shown in FIGS. 7A-9B of U.S. Patent Application Publication 2016/0081810. In some embodiments, a coupling device may be attached to the proximal end of any of the implants shown in FIGS. 11-27 of U.S. Patent Application 62/649,466. In some embodiments, the proximal ends of two or more implants may be joined together with a bridging structure that includes a coupling device for attaching to a spinal rod. In some embodiments, an implant can resemble a staple with two or more prongs for inserting into bone, the implant having a coupling device located on its proximal end.

Figure 25A:
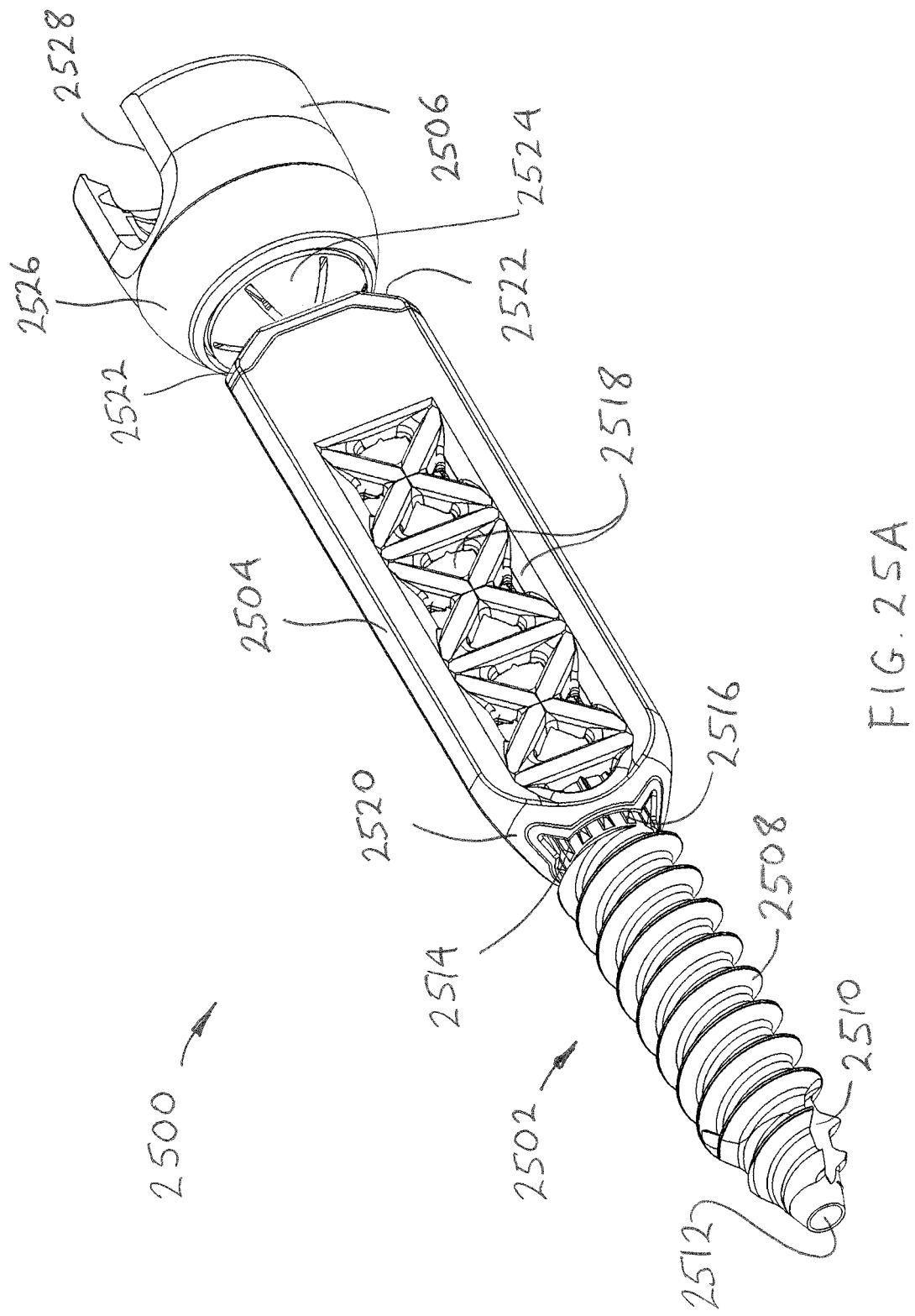
FIG. 25A is a perspective view showing an exemplary embodiment of a bone implant having a tulip or coupling device provided at its proximal end.
Figure 25B:
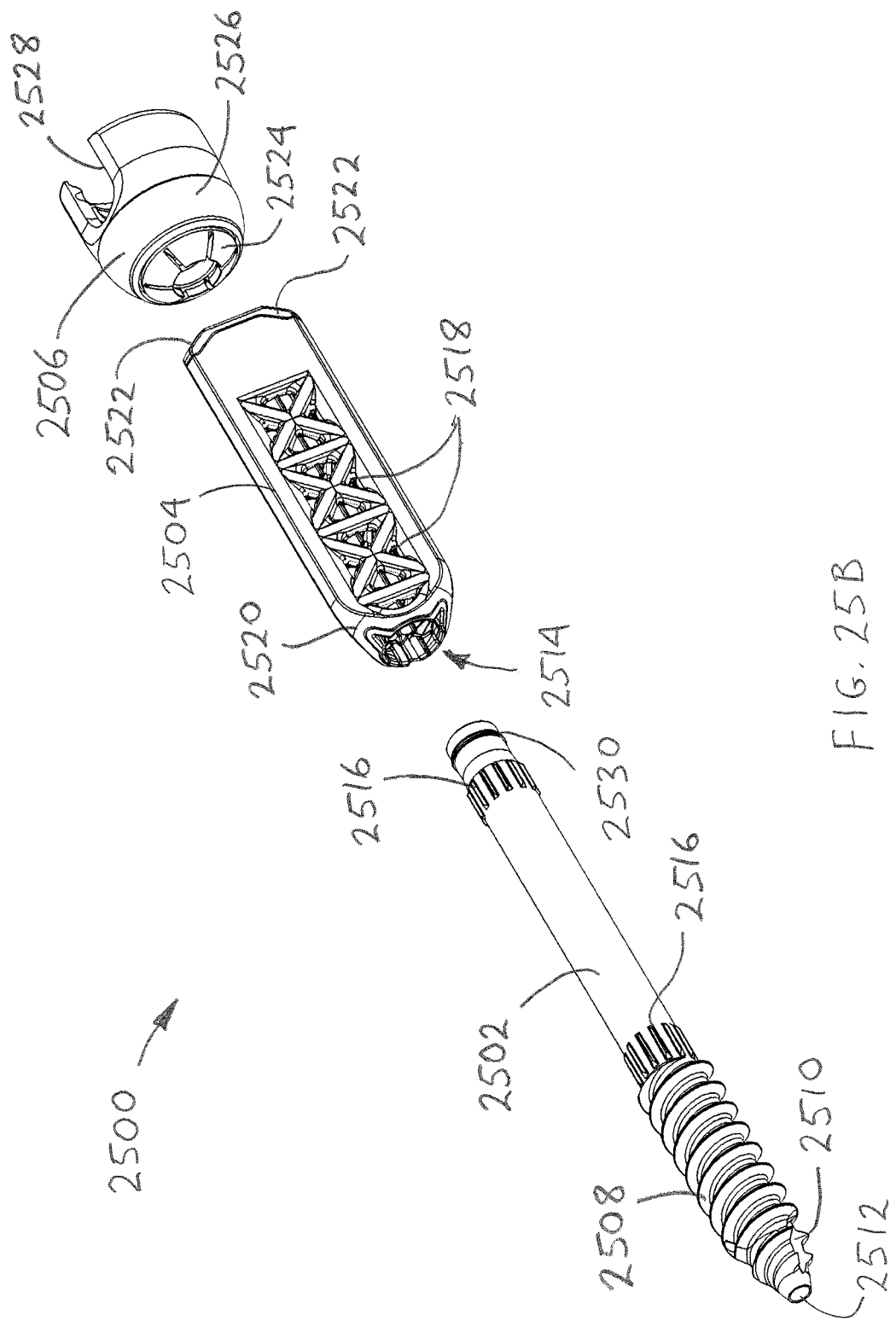
FIG. 25B is an exploded view showing the components of the bone implant of FIG. 25A.
Figure 25C:
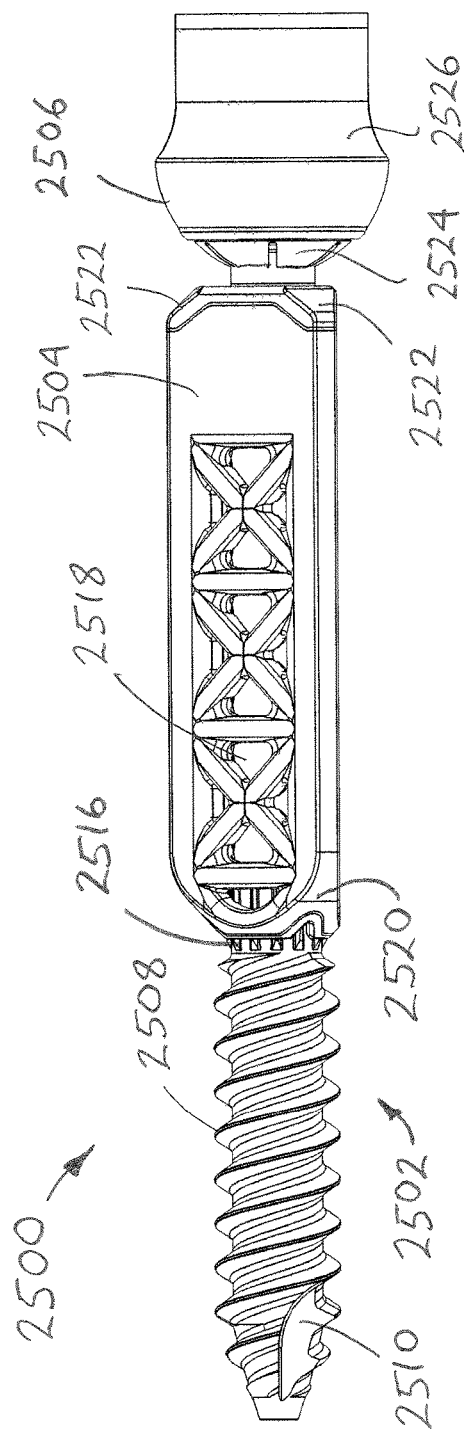
FIG. 25C is a side view showing the bone implant of FIG. 25A.
Figure 25D:
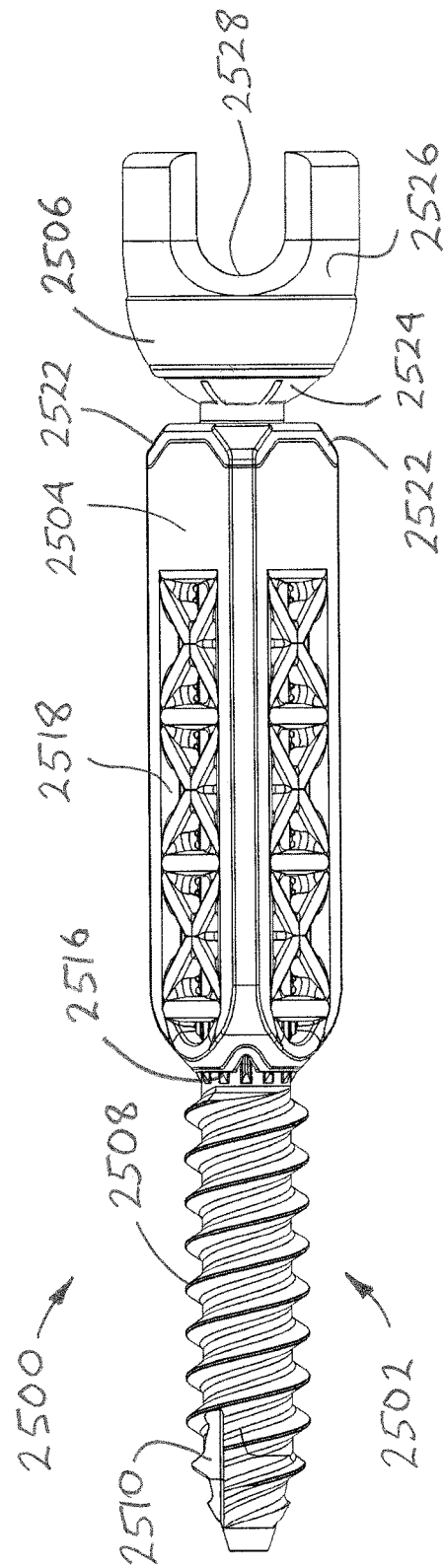
FIG. 25D is a top plan view showing the bone implant of FIG. 25A.
Figure 25E:
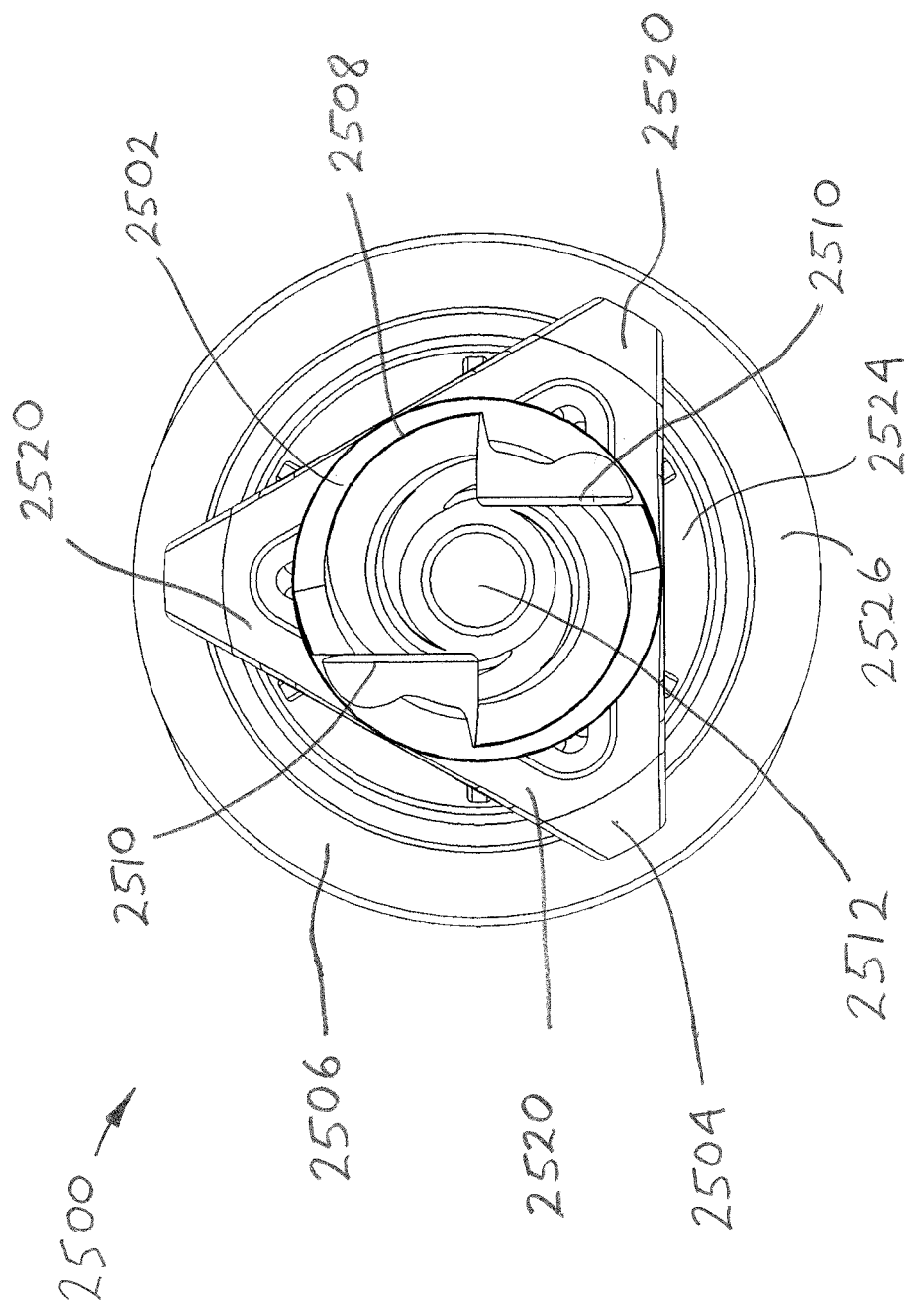
FIG. 25E is a distal end view showing the bone implant of FIG. 25A.

FIGS. 25A-25G show another exemplary embodiment of a bone implant having a tulip or coupling device provided at its proximal end. As best seen in FIG. 25B, implant 2500 includes a shank portion 2502, a body portion 2504 and a head portion 2506. In this embodiment, the distal end of shank portion 2502 includes threads 2508 for threading the shank portion 2502 into a bone segment. Threads 2508 may include one or more self-tapping cutouts 2510, as best seen in FIG. 25E. The proximal end of shank portion 2502 may be provided with a hexagonal recess (not shown) or other suitable feature to mate with a driver to screw the shank portion 2502 into the bone segment. A central lumen 2512 may be provided along the longitudinal axis of shank portion 2502 to allow it to be placed over a guidewire or guide pin when being implanted.

In this embodiment, body portion 2504 is provided with a central lumen 2514 configured to slide over the proximal end of shank portion 2502. Radially outward extending splines 2516 may be provided at one or more locations on shank portion 2502, as best seen in FIG. 25B, to mate with corresponding grooves along the inner surface of central lumen 2514. Splines 2516 and/or other non-rotating features may be provided on shank portion 2502 and body portion 2504 to prevent the two parts from rotating relative to one another. Splines 2516 and or their corresponding grooves may be tapered to create a tight fit when body portion 2504 is tapped into place over shank portion 2502. Splines may be omitted in the middle of shank portion 2502 as shown to reduce stress concentrations and thereby increase fatigue properties of the implant. In other embodiments (not shown), these non-rotation features may be omitted to permit body portion 2504 to rotate relative to shank portion 2502.

In this embodiment, body portion 2504 has a triangular cross-section to prevent it from rotating relative to surrounding bone. When body portion 2504 is placed across a joint or fracture between two bone segments as previously described, body portion 2504 inhibits the two bone segments from rotating or translating relative to one another. In other embodiments (not shown), the body portion may have a square, rectangular, oval or other cross-sectional shape with at least one rectilinear face and/or at least one apex to similarly prevent rotation. When body portion 2504 is prevented from rotating relative to the surrounding bone by virtue of its non-rotationally shaped cross-section, and when splines 2516 prevent shank portion 2502 from rotating relative to body portion 2504, shank portion 2502 is prevented from rotating relative to the surrounding bone. This arrangement prevents shank portion 2502 from undesirably backing out or migrating further into the bone.

Body portion 2504 may be provided with fenestrations 2518 to allow for bony on-growth, in-growth and through-growth. In this exemplary embodiment, a repeating pattern of spars and cross-struts creates a plurality of triangularly shaped fenestrations on each face of body portion 2504. Each of the fenestrations 2518 opens into the central lumen 2514 of body portion 2504. In some embodiments, body portion 2504 is fabricated using an additive manufacturing process such as 3D printing. Further information on designing and manufacturing fenestrated implants is provided in the applicant's U.S. Pat. No. 9,662,157, filed Sep. 18, 2015, and titled "Matrix Implant." The distal end of body portion 2504 may also be provided with tapered and rounded leading edges 2520 as shown to facilitate inserting body portion 2504 into one or more bone segments. Trailing edges 2522 having a lesser degree of taper may be provided on the proximal end of body portion 2504 as shown to facilitate removal of body portion 2504 from the bone, if desired. Having less taper on trailing edges 2522 permits better engagement between the proximal end and surrounding cortical bone surfaces.

Head portion 2506 may be provided with a coupler 2524 and a main body 2526 as shown in FIGS. 25A-25E, and a nut (not shown). The nut has external threads that mate with internal threads located in the proximal recess of main body 2526 to tighten a spinal rod (not shown) against the bottom of channels 2528 in main body 2526. As shown in FIG. 25B, the proximal end of shank portion 2502 may be provided with a circumferential rib or barb 2530 for securing head portion 2506 to shank portion 2502 in a snap-fit manner. In some embodiments, main body 2526 is configured to pivot in a poly-axial or spherical manner relative to coupler 2524 and shank portion 2502. In some embodiments, main body 2526 is configured to spin about its main axis relative to coupler 2524 and shank portion 2502. In some embodiments, main body 2526 is configured to immovable relative to coupler 2524 and/or shank portion 2502.

Referring to FIGS. 25F and 25G, central lumen 2514 of body portion 2504 and/or shank portion 2502 may be configured to reduce stress concentrations on shank portion 2502 to help ensure it does not fail in use after it has been implanted. In some prior art implants, repetitive heavy load cycles on the proximal end of shank portion 2502 from a spinal rod connected to the head portion can cause the shank portion to break apart. A typical point of failure is where the shank portion 2502 exits the proximal end of the body portion 2504. According to aspects of the present disclosure, stress concentrations may be reduced in this area to permit greater load cycling without implant failure.

In some embodiments, as shown in FIG. 25F, the proximal end of central lumen 2514 of body portion 2504 may be provided with a curved contour 2532 as shown to more evenly distribute forces between shank portion 2502 and body portion 2504, thereby reducing stress concentrations. In FIG. 25F, the proximal end of shank portion 2502 is depicted in an unloaded state with solid lines and in a deflected state with dashed lines. The degree of deflection is exaggerated in FIG. 25F for ease of understanding. Curved contour 2532 may be provided on just one side of central lumen 2514 in the direction of maximum force, on opposite sides of central lumen 2514, or around the entire circumference of central lumen 2514. In some embodiments, curved contour 2532 may mirror the natural bending profile of shank portion 2502. In particular, the contour may be defined by the following beam deflection formulas:

$$y = (F \cdot x^2)/(6 \cdot E \cdot I)(x - 3 \cdot l)$$

$$I = (D^4 - d^4)\pi/64$$

where
x=distance in horizontal direction in FIG. 25F
y=distance in vertical direction in FIG. 25F
F=force applied to proximal end of shank portion 2502
E=modulus of elasticity of shank portion 2502
I=moment of inertia of shank portion 2502
l=length between where shank portion 2502 is fully supported and the point of force application
D=outside diameter of shank portion 2502
d=inside diameter of shank portion 2502

In some embodiments, as shown in FIG. 25G, shank portion 2502' may be provided with a spherical portion 2534 and body portion 2504' may be provided with a mating spherical socket. Body portion 2504' may also be provided with a central lumen 2514' that tapers outwardly towards both its proximal and distal ends, as shown. With this arrangement, shank portion 2502' may pivot within body portion 2504' when a force is applied to its proximal end. The tapered portions may be provided on just one side of central lumen 2514' in the direction of maximum force, on opposite sides of central lumen 2514', or around the entire circumference of central lumen 2514'. When shank portion 2502' reaches the end of its pivoting travel, it is supported by a large surface area of body portion 2504' at both the proximal and distal ends, and may also be supported at spherical portion 2534. These large areas of support greatly reduce the stress concentrations found in prior art implants, and allow the implant to withstand greater forces and/or a larger number of loading cycles without failure. In the embodiments of FIGS. 25F and 25G, the outer surface of shank portion 2502/2502' and/or the inner surface of body portion 2504/2504' may be highly polished to further reduce stress concentrations. In some embodiments the surfaces may have a roughness Ra of between 0.01 and 0.04 microns.

Implant 2500/2500' may be installed in bone, such as across a bone joint or fracture, in a manner similar to that previously described relative to FIGS. 2A-2F and FIG. 24 (i.e. in an S2AI trajectory). In particular, the bone may be prepared by inserting a guide pin into bone segments, spinning a cannulated drill over the guide pin to drill a pilot hole in the bone, and tapping a cannulated broach over the guide pin to create a bore shaped to receive body portion 2504. In some embodiments, any or all of these steps may be omitted. Shank portion 2502 may then be threaded into the pilot hole using a tool attached to the proximal end of shank portion 2502, as previously described. Body portion 2504 may then be tapped into the bone over the proximal end of shank portion 2502. As body portion 2504 engages the splines 2516 located on the proximal end of shank portion 2502, a small rotational adjustment (no more than 15 degrees, for example), may be needed to rotationally align body portion 2504 with the shaped bore. This adjustment may be made manually, or in some circumstances may occur automatically as the tapered and rounded leading edges 2520 of body portion 2504 engage the shaped bore opening in the bone and automatically rotate the implant as needed while body portion 2504 is being tapped into place. Once body portion 2504 is in place, head portion 2506 may be snapped into place on the proximal end of shank portion 2502. Head portion 2506 may include proximally extending tabs as previously described that may be snapped off at this time. When other portions of a spinal construct (not shown) are also in place, a rod may be placed into channels 2528 and secured in place with a nut, as previously described.

In embodiments having a separate head portion that is assembled to a shank portion during implantation as described above, a variety of different head portions can be provided in a kit without having to provide the entire implant for each head type. For example, head portions can be provided that couple to a 5.0, 5.5, 6.0, or 6.35 mm diameter rod. Shank portions and body portions may also be provided in various lengths, widths and or shapes. With this modular approach, a specific head type may be assembled to a specific shank portion and body portion to create a greater number of combinations without having to stock a separate implant for each combination.

In some embodiments, shank portion 2502 can be installed in the bone, and then a broach can be inserted over the proximal end of installed shank portion 2502 to create a shaped bore. After the broach is removed, body portion 2504 may then be installed over shank portion 2502. In some embodiments, the body portion may include an integrated broach such that the body portion can be installed without first preparing a shaped bore in the bone. In some embodiments, body portion 2504 can be installed in the bone first, and then shank portion 2502 can be installed into the bone through body portion 2504, with or without head portion 2506 attached to shank portion 2502 as it is being installed.

According to aspects of the present disclosure, the arrangement of the current embodiment allows for one portion of an implant to be screwed into place, another portion to be tapped into place, and the two portions locked together to take advantage of the anti-rotational aspects of the tapped in portion. In embodiments without splines or other locking features, the various portions can be implanted separately as previously described, or the assembled implant can be installed as a single unit with the body portion rotating in a shaped bore in the bone as the shank portion is screwed into place. In other embodiments having releasable locking features (not shown), the assembled implant can be installed as a single unit with the locking feature released, allowing the shank portion to rotate relative to the body portion. After the implant is installed, the locking feature can be engaged to prevent rotation.

FIGS. 26A-26E show another exemplary embodiment of a bone implant having a tulip or coupling device provided at its proximal end. Implant 2600 includes a shank portion 2602, a body portion 2604 and a head portion 2606. Shank portion 2602 and body portion 2604 may be separate components as with previously described implant 2500, or they may be integrally formed as a single component. In this embodiment, the distal end of shank portion 2602 includes bristles 2608 for securing the shank portion 2602 into a bone segment. Bristles 2608 may be angled proximally and may be flexible, thereby providing little resistance when being introduced distally into a bore within a bone, but locking against the bone and preventing proximal withdrawal from the bone. In some embodiments, bristles 2608 are arranged at a 45 degree angle relative to the longitudinal axis of the implant 2600. Bristles 2608 may be integrally formed with shank portion 2602, such as with an additive manufacturing process. Alternatively, bristles 2608 may be separate elements of the same or different material from shank portion 2602 and inserted into holes formed in shank portion 2602. In some embodiments, head portion 2606 serves to contact the outer surface of the bone to prevent implant 2600 from migrating further into the bone. In other embodiments (not shown), another element that is larger in size than the implant bore in the bone may be located on or adjacent to the proximal end of body portion 2604 to prevent implant 2600 from migrating further into the bone while allowing head portion 2606 to maintain a full range of motion relative to shank portion 2602. In other embodiments (not shown), bristles 2608 may be replaced with or augmented by rigid barbed elements. Further details relating to the fabrication and use of bristles and barbs with orthopedic implants may be found in U.S. Pat. No. 5,716,358 to Ochoa et al.

The proximal end of body portion 2604 may be provided with a flat surface (not shown) to allow shank portion 2602 and body portion 2604 to be tapped into place together into the bone segment(s). Alternatively, internal threads (not shown) may be provided to allow a slap-hammer or other insertion instrument to be temporarily attached to the proximal end of body portion 2604 to aid in inserting implant 2600. A central lumen 2612 may be provided along the longitudinal axis of shank portion 2602 and body portion 2604 to allow them to be placed over a guidewire or guide pin when being implanted.

In this embodiment, body portion 2604 has a triangular cross-section to prevent it from rotating relative to surrounding bone. When body portion 2604 is placed across a joint or fracture between two bone segments as previously described, body portion 2604 inhibits the two bone segments from rotating relative to one another. In other embodiments (not shown), the body portion may have a square, rectangular, oval or other cross-sectional shape with at least one rectilinear face and/or at least one apex to similarly prevent rotation.

Body portion 2604 may be provided with fenestrations 2618 to allow for bony on-growth, in-growth and through-growth. In this exemplary embodiment, a repeating pattern of alternating triangularly shaped fenestrations may be provided on each face of body portion 2604. Each of the fenestrations 2618 opens into a central lumen of body portion 2604. In some embodiments, body portion 2604 is fabricated using an additive manufacturing process such as 3D printing. Further information on designing and manufacturing fenestrated implants is provided in the applicant's U.S. Pat. No. 9,662,157, filed Sep. 18, 2015, and titled "Matrix Implant." The distal end of body portion 2604 may also be provided with tapered leading edges 2620 as shown to facilitate inserting body portion 2604 into one or more bone segments. Trailing edges 2622 having a lesser degree of taper may be provided on the proximal end of body portion 2604 as shown to facilitate removal of body portion 2604 from the bone, if desired. Having less taper on trailing edges 2622 permits better engagement between the proximal end and surrounding cortical bone surfaces.

Figure 26A:
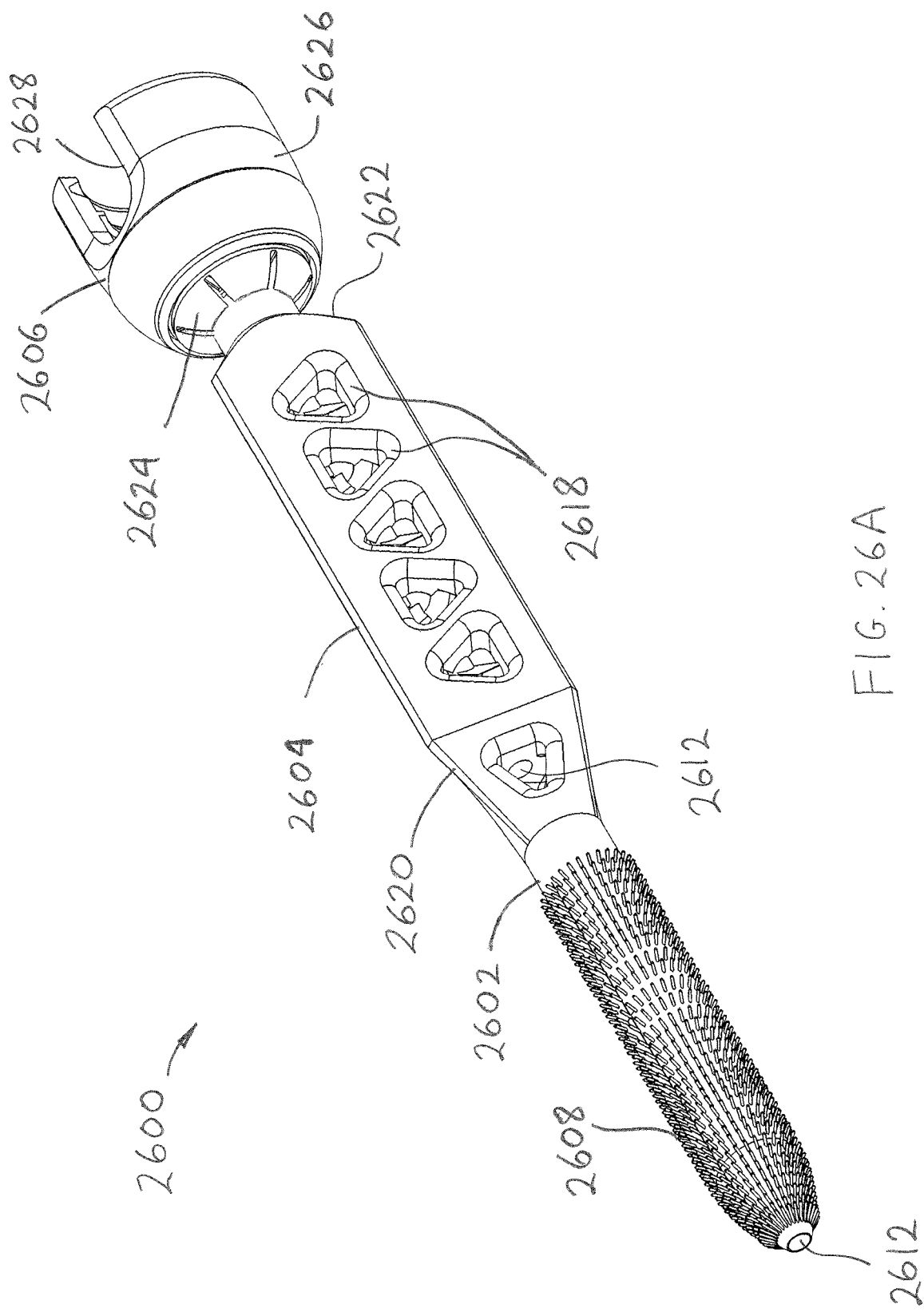
FIG. 26A is a perspective view showing an exemplary embodiment of a bone implant having a tulip or coupling device provided at its proximal end.
Figure 26B:
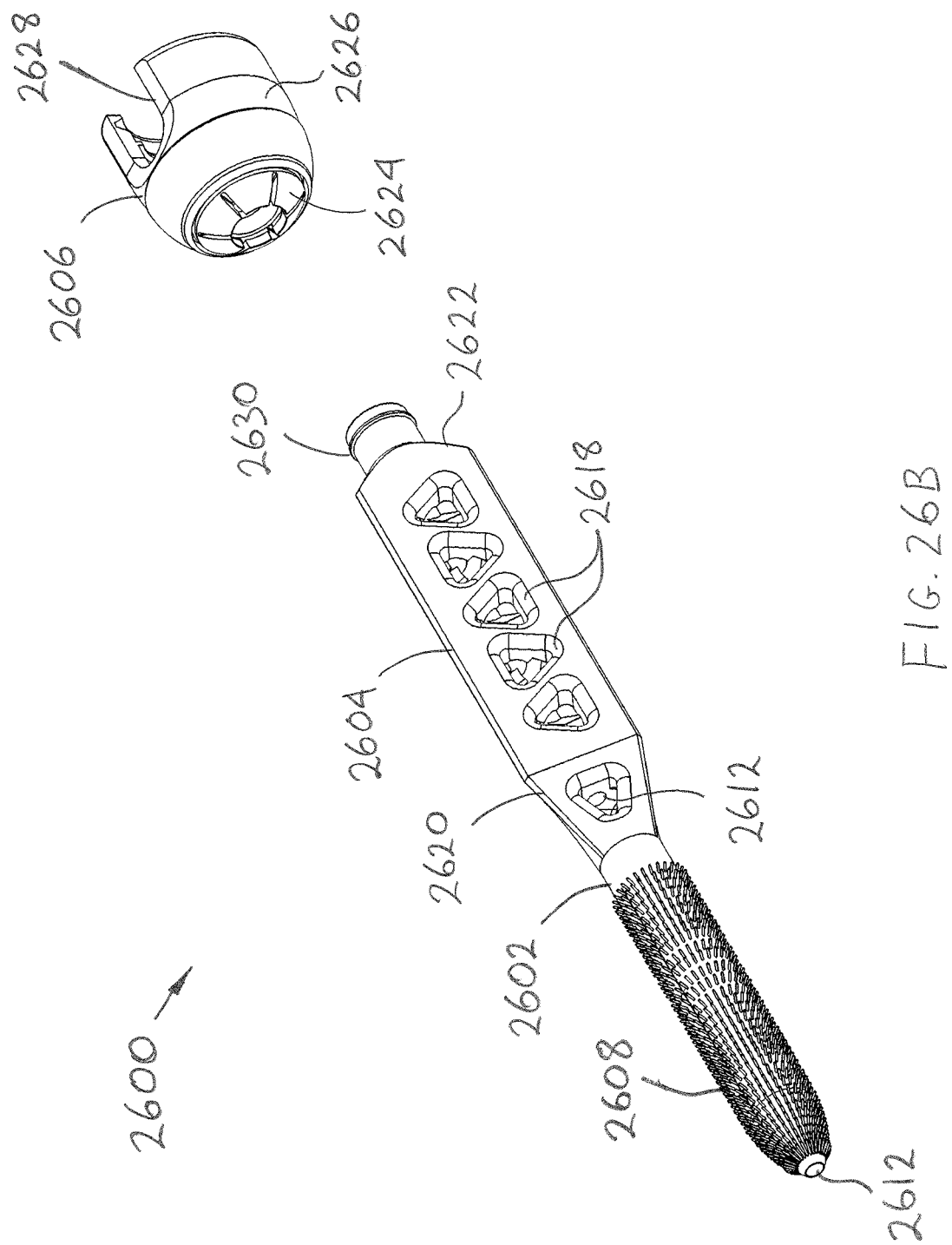
FIG. 26B is an exploded view showing the components of the bone implant of FIG. 26A.
Figure 26C:
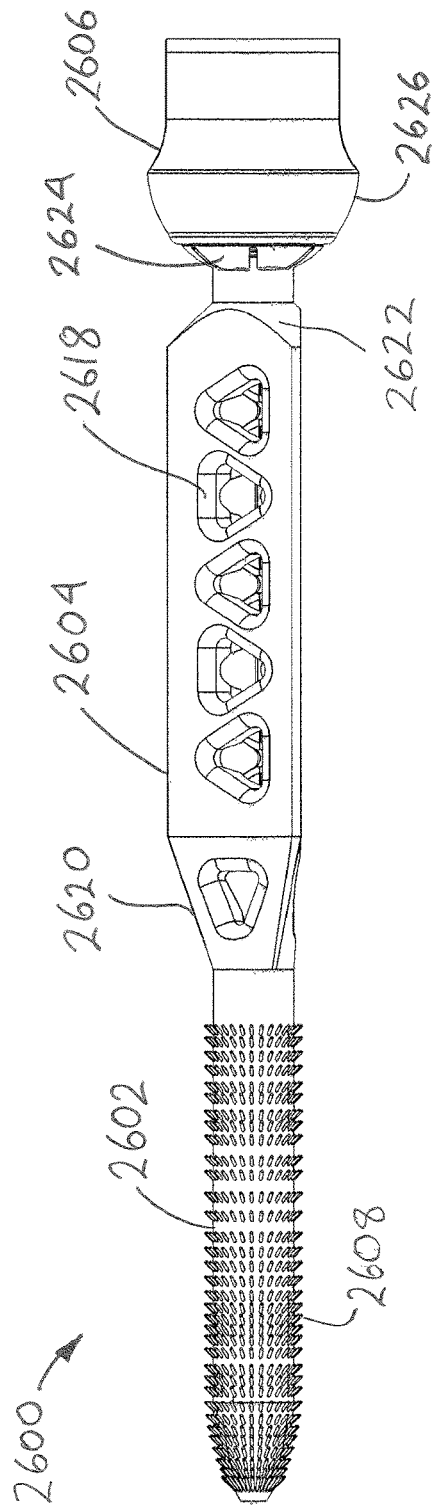
FIG. 26C is a side view showing the bone implant of FIG. 26A.
Figure 26D:
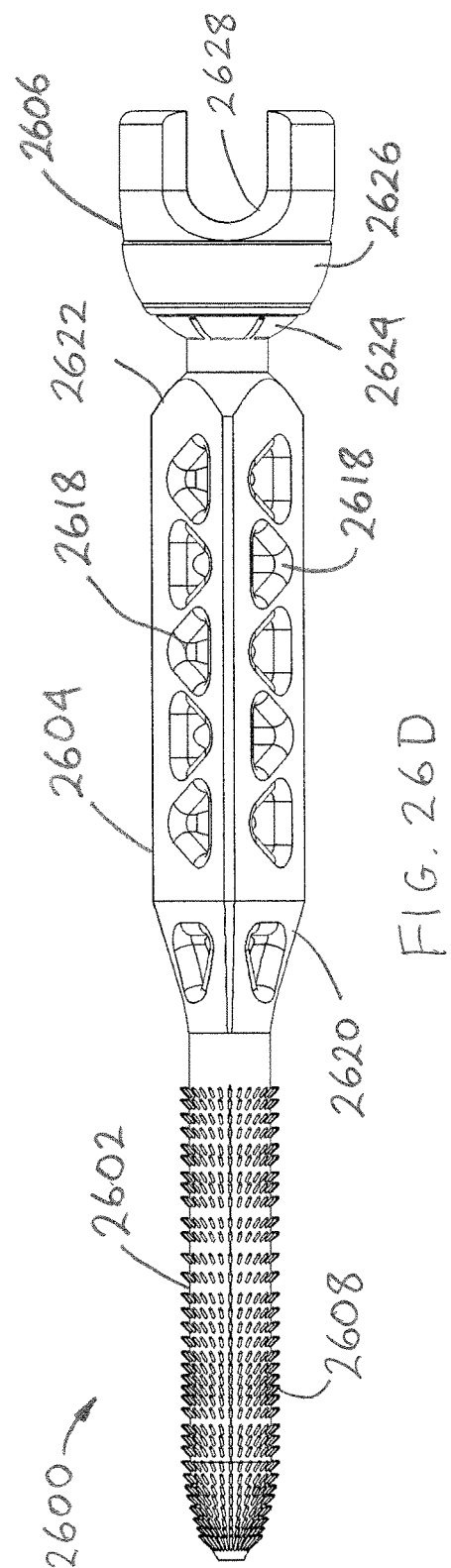
FIG. 26D is a top plan view showing the bone implant of FIG. 26A.
Figure 26E:
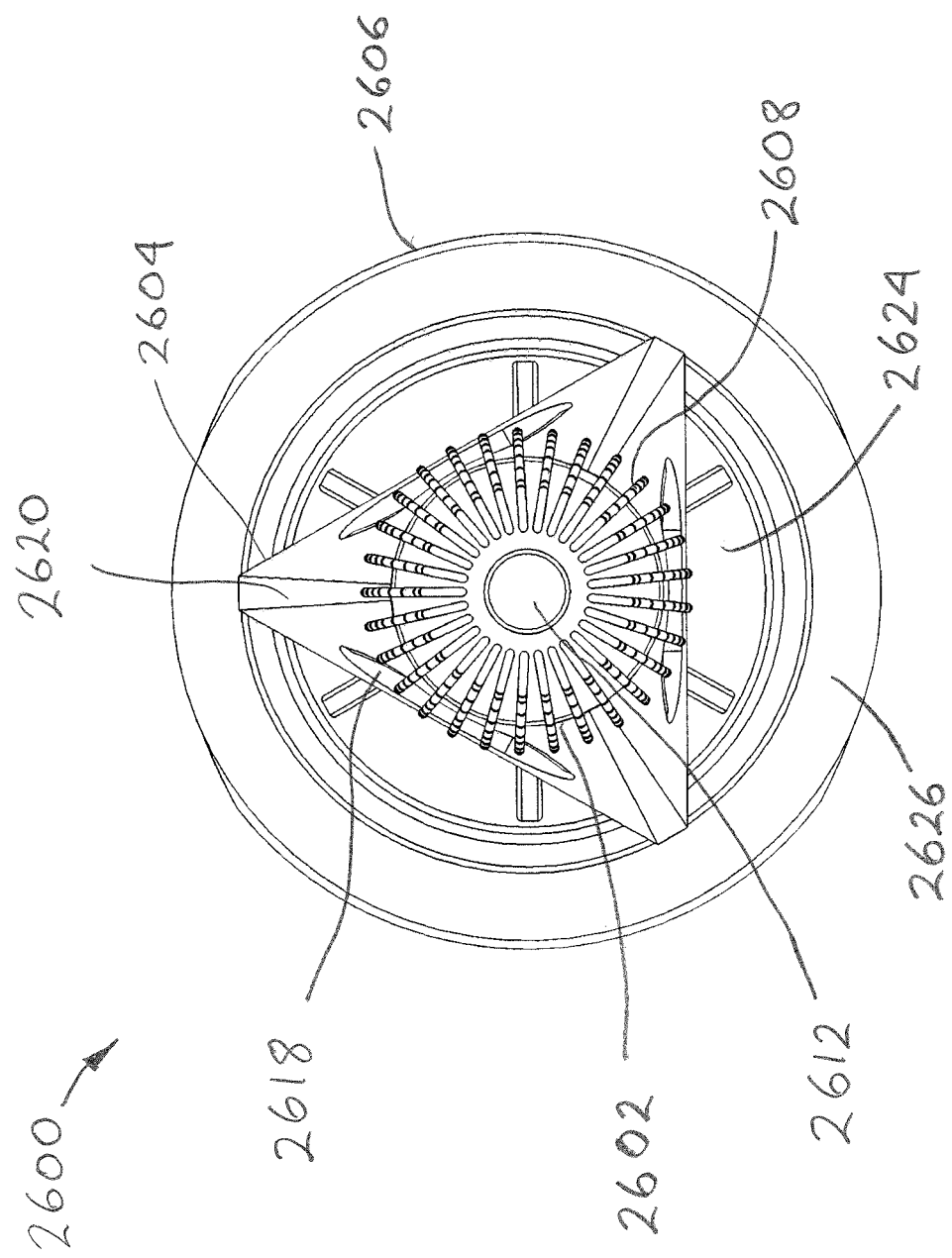
FIG. 26E is a distal end view showing the bone implant of FIG. 26A.

Head portion 2606 may be provided with a coupler 2624 and a main body 2626 as shown in FIGS. 26A-26E, and a nut (not shown). The nut has external threads that mate with internal threads located in the proximal recess of main body 2626 to tighten a spinal rod (not shown) against the bottom of channels 2628 in main body 2626. As shown in FIG. 26B, the proximal end of body portion 2604 may be provided with a circumferential rib or barb 2630 for securing head portion 2606 to body portion 2604 in a snap-fit manner. In some embodiments, main body 2626 is configured to pivot in a poly-axial or spherical manner relative to coupler 2624 and shank portion 2602. In some embodiments, main body 2626 is configured to spin about its main axis relative to coupler 2624 and shank portion 2602. In some embodiments, main body 2626 is configured to immovable relative to coupler 2624 and/or body portion 2604.

Implant 2600 may be installed in bone, such as across a bone joint or fracture, in a manner similar to that previously described relative to FIGS. 2A-2F. In particular, the bone may be prepared by inserting a guide pin into bone segments, spinning a cannulated drill bit over the guide pin to drill a pilot hole in the bone, and tapping a cannulated broach over the guide pin to create a bore shaped to receive body portion 2604. In some embodiments, any or all of these steps may be omitted. Shank portion 2602 and body portion 2604 may then be tapped into the pilot hole and shaped bore, with or without a tool attached to the proximal end of body portion 2604, as previously described. Once shank portion 2602 and body portion 2604 are in place, head portion 2606 may be snapped into place on the proximal end of body portion 2604. In some implementations, shank portion 2602 and body portion 2604 may be tapped into place with head portion 2606 already installed on the proximal end of body portion 2604. Head portion 2606 may include proximally extending tabs as previously described that may be snapped off at this time. When other portions of a spinal construct (not shown) are also in place, a rod may be placed into channels 2628 and secured in place with a nut, as previously described.

FIGS. 27A and 27B show another exemplary embodiment of a bone implant having a tulip or coupling device provided at its proximal end. Implant 2700 is a form of sacral alar iliac (SAI) screw and includes a threaded shank portion 2702, a body portion 2704 and a head portion 2706. Threaded shank portion 2702 and head portion 2706 of implant 2700 are similar to those of implant 2500 previously described in reference to FIGS. 25A-25G.

Body portion 2704 includes a porous exterior surface that is configured to reside across a bone joint and/or a proximal bone segment when implanted. In this embodiment, body portion 2704 includes a radially inward portion 2708 that is solid and a radially outward portion 2710 that is a porous bony in-growth region, as shown in FIG. 27B. Radially outward portion 2710 may be formed from a porous plasma spray coating with an irregular surface, which supports stable bone fixation/fusion. This implant structure and the surgical approaches disclosed herein make possible the placement of larger fusion surface areas designed to maximize post-surgical weight bearing capacity and provide a biomechanically rigorous implant designed specifically to stabilize the heavily loaded SI-Joint. In other embodiments, the entire shank portion and body portions can be porous.

Implant 2700 can be made of a variety of materials. For example, the implant can be made of a metal or metal alloy, such as titanium or steel, or a nonmetallic material such as ceramic or polymer. In some embodiments, the implant material can have a certain lattice microstructure formed from microparticles. For example, the lattice microstructure can result in a rough or smooth surface texture, depending on the surface finishing techniques used, such as polishing or application of a metal plasma spray. A 3-D printing process may be used to fabricate some or all of implant 2700, which allows the porosity of the implant or printed portions to be controlled. For example, the implant can have a volume porosity between about 30 and 70 percent, with an average pore size between 100 and 1000 microns. The pores can be largely interconnected, largely unconnected, or a mix of interconnected and unconnected pores. In some embodiments, the pores can be located throughout the material of the implant, including the inner and outer implant surfaces. For example, the fusion of the microparticles that form the implant can result in a porous, semi-porous, or nonporous structure, depending on the degree of fusion between the microparticles. In other embodiments, the pores can be located in a porous coating that can be applied onto the implant. For example, a porous coating can be applied using a titanium plasma spray process, or another metal plasma spray process. The coating can be applied to the outer surfaces of the implant, the interior surfaces of the implant, or both the outer and interior surfaces of the implant. For example, the coating could be preferentially applied to the outer surface of a matrixed implant to provide bony ingrowth and on-growth, and not applied to the inner portion of the implant to maximize bony through-growth within the implant. Also, the coating can be applied preferentially from proximal to distal, or vice versa. The thickness of a porous coating can be between about 500 and 1,500 microns. In addition or alternatively to the porous metal coating, a hydroxyapatite coating can also be applied to the implant. In some embodiments, the porosity can be varied along the length of the implant. In some embodiments, the thickness of the coating can be varied along the length of the implant. In some embodiments, the thickness of the coating applied to the outer surface can be different than the thickness of the inner coating. For example, the outer coating may be greater than the inner coating in some embodiments. In other embodiments, the thickness of the inner and outer coatings can be the same.

FIGS. 28A and 28B show another exemplary embodiment of a bone implant having a tulip or coupling device provided at its proximal end. Implant 2800 is a form of sacral alar iliac (SAI) screw and includes a threaded shank portion 2802, a body portion 2804 and a head portion 2806. Threaded shank portion 2802 and head portion 2806 of implant 2800 are similar to those of implant 2500 previously described in reference to FIGS. 25A-25G.

Body portion 2804 includes a porous exterior surface that is configured to reside across a bone joint and/or a proximal bone segment when implanted, and may be similar to body portion 2704 previously described in reference to FIGS. 27A and 27B. In this embodiment, body portion 2804 includes fenestrations 2808 that communicate between the exterior surface and a central lumen 2810. Fenestrations 2808 may be circular in shape as shown, or may be formed in other shapes. Fenestrations 2808 may be configured to promote bony on-growth, ingrowth and/or through-growth for faster implant and/or bone joint fusion.

Figure 29A:
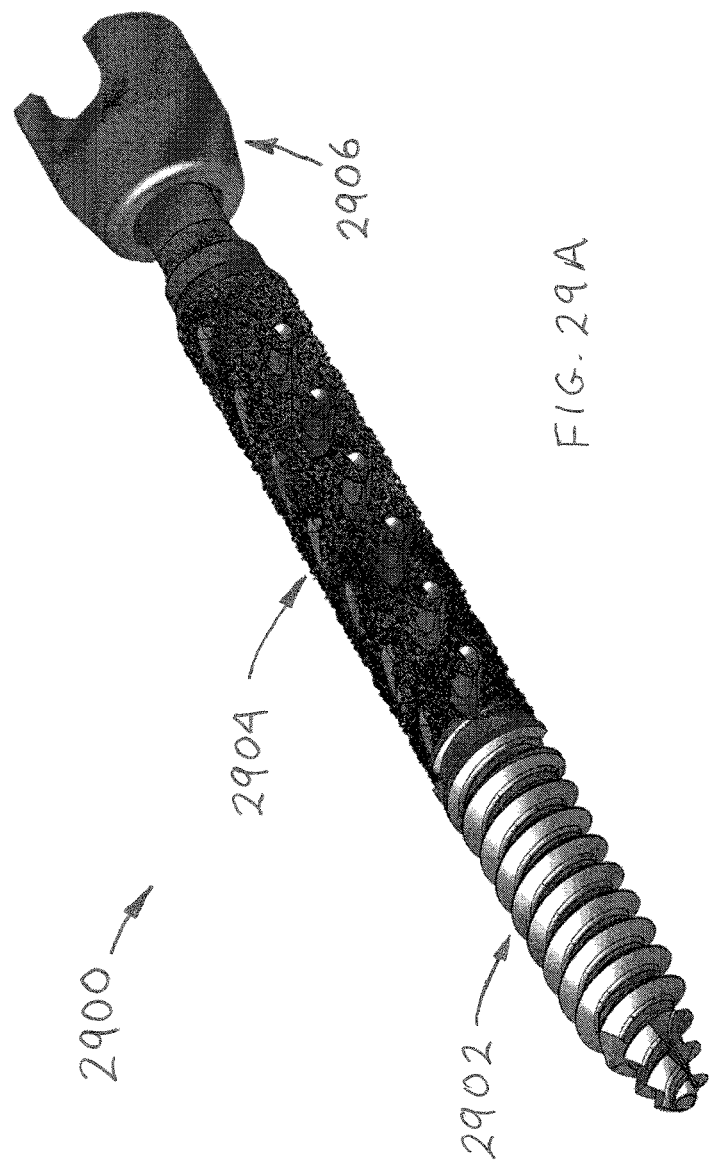
FIG. 29A is a perspective view showing an exemplary embodiment of a bone implant having a tulip or coupling device provided at its proximal end.
Figure 29B:
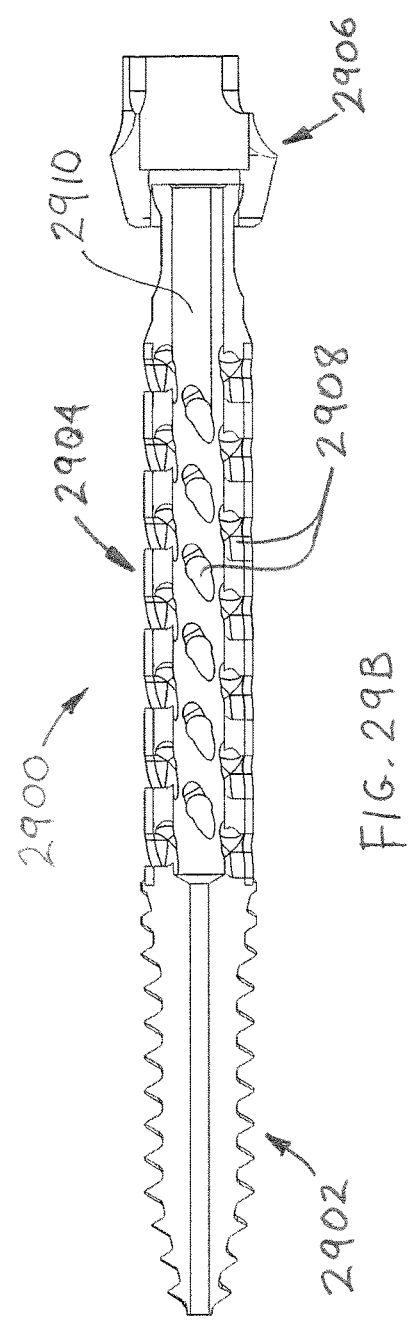
FIG. 29B is a side sectional view showing the bone implant of FIG. 29A.

FIGS. 29A and 29B show another exemplary embodiment of a bone implant having a tulip or coupling device provided at its proximal end. Implant 2900 is a form of sacral alar iliac (SAI) screw and includes a threaded shank portion 2902, a body portion 2904 and a head portion 2906. Threaded shank portion 2902 and head portion 2906 of implant 2900 are similar to those of implant 2500 previously described in reference to FIGS. 25A-25G.

Body portion 2904 includes a porous exterior surface that is configured to reside across a bone joint and/or a proximal bone segment when implanted, and may be similar to body portion 2704 previously described in reference to FIGS. 27A and 27B. In this embodiment, body portion 2904 includes fenestrations 2908 that communicate between the exterior surface and a central lumen 2910. Fenestrations 2908 may be oblong and set at an angle, as shown. In this exemplary embodiment, fenestrations 2908 are all aligned in the same direction as the threads located on the shank portion 2902, but form a more acute angle with the longitudinal axis of implant 2900. Additionally, fenestrations 2908 may be provided with sharp cutting edges, such as along their proximal and/or trailing edges. These cutting edges can scrape bone material from the surrounding bone as implant 2900 is being screwed into place and channel the bone material towards central lumen 2910 to create a self-grafting SAI screw. This bone material may then promote faster bone growth in and/or around implant 2900. Fenestrations 2908 themselves may also promote bony on-growth, ingrowth and/or through-growth for faster implant and/or bone joint fusion.

FIGS. 30A and 30B show another exemplary embodiment of a bone implant having a tulip or coupling device provided at its proximal end. Implant 3000 is a form of sacral alar iliac (SAI) screw and includes a threaded shank portion 3002, a body portion 3004 and a head portion 3006. Threaded shank portion 3002 and head portion 3006 of implant 3000 are similar to those of implant 2500 previously described in reference to FIGS. 25A-25G.

Body portion 3004 includes a porous exterior surface that is configured to reside across a bone joint and/or a proximal bone segment when implanted, and may be similar to body portion 2704 previously described in reference to FIGS. 27A and 27B. In this embodiment, a single set of threads 3008 extends continuously across shank portion 3002 and body portion 3004. On the body portion 3004, the minor diameter or roots of threads 3008 may be filled with or formed by a porous material 3010. The major diameter or crests of threads 3008 may be formed on top of a sleeve of porous material 3010, as shown in FIG. 30B. Alternatively, the major diameter or crests of threads 3008 may be formed integrally with the minor diameter or roots, and the porous material 3010 can simply reside within the roots (not shown.) Porous material 3010 may then promote on-growth to body portion 3004 and in-growth to threads 3008.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An implant for use in fusing and or stabilizing a plurality of bones, the implant comprising:
    a shank portion having a proximal end and a distal end comprising one or more threads for securing the implant to a second bone segment;
    a body portion sized and configured to be positioned over at least a portion of the shank portion, the body portion having a distal region that is coupled to the shank portion to prevent motion therebetween in at least one direction, the body portion having a central region that is proximal to the distal region, the central region uncoupled from a central region of the shank portion when the distal region of the body portion is coupled to the shank portion,
    the body portion configured to be placed through a first bone segment, across a bone joint or fracture and into the second bone segment, the body portion including a plurality of fenestrations therethrough and configured to allow for bony on-growth, ingrowth and through-growth, and
    a head portion coupled to the proximal end of the shank portion and configured to couple the shank portion to a stabilizing rod.

2. The implant of claim 1, wherein the first bone segment is a sacrum and the second bone segment is an ilium.

3. The implant of claim 1, wherein the body portion comprises at least one rectilinear face to prevent rotation.

4. The implant of claim 1, wherein the body portion has a cross-section transverse to a longitudinal axis that is triangular in shape to prevent rotation.

5. The implant of claim 1, wherein the body portion comprises at least one apex to prevent rotation.

6. The implant of claim 1, wherein the shank portion comprises at least one spline that mates with at least one slot within the distal region of the body portion to prevent relative rotation between the shank portion and the body portion.

7. The implant of claim 1, wherein the shank portion includes one or more elongate movement resisting elements extending along the shank portion that are configured to mate with one or more recessed elements in an inner surface of the distal region of the body portion to prevent motion between the shank portion and the body portion in the at least one direction, wherein the one or more elongate movement resisting elements do not extend into the central region of the shank portion.

8. The implant of claim 7, wherein the one or more elongate movement resisting elements are sized and configured to form a tight fit with the one or more recessed elements in the inner surface of the distal region of the body portion.

9. The implant of claim 7, wherein the one or more elongate movement resisting elements extend axially along the shank portion.

10. An implant for use in fusing and or stabilizing a plurality of bones, the implant comprising:
- a shank portion having a proximal end and a distal end comprising one or more threads;
- a body portion sized and configured to be positioned over at least a portion of the shank portion, the body portion having a distal region that is coupled to the shank portion to prevent motion therebetween in at least one direction, the body portion having a central region that is proximal to the distal region, the central region uncoupled from a central region of the shank portion when the distal region of the body portion is coupled to the shank portion,
- the body portion configured to be placed into a first bone segment, the body portion including a plurality of fenestrations therethrough and configured to allow for bony on-growth, ingrowth and through-growth and
- a head portion coupled to the proximal end of the shank portion and configured to couple the shank portion to a stabilizing rod.

11. The implant of claim 10, wherein the first bone segment is a vertebra.

12. The implant of claim 10, wherein the first bone segment is a sacrum.

13. The implant of claim 10, wherein the first bone segment is an ilium.

14. The implant of claim 10, wherein the body portion comprises at least one rectilinear face to prevent rotation.

15. The implant of claim 10, wherein the body portion has a cross-section transverse to a longitudinal axis that is triangular in shape to prevent rotation.

16. The implant of claim 10, wherein the body portion comprises at least one apex to prevent rotation.

17. The implant of claim 10, wherein the shank portion comprises at least one spline that mates with a slot within the distal region of the body portion to prevent relative rotation between the shank portion and the body portion.

18. The implant of claim 10, wherein the shank portion includes one or more elongate movement resisting elements that are configured to mate with one or more recessed elements on an inner surface of the distal region of the body portion to prevent motion between the shank portion and the body portion in the at least one direction, wherein the one or more elongate movement resisting elements do not extend into the central region of the shank portion.

19. The implant of claim 18, wherein the one or more elongate movement resisting elements are sized and configured to form a tight fit with the one or more recessed elements in the inner surface of the distal region of the body portion.

20. The implant of claim 18, wherein the one or more elongate movement resisting elements extend axially along the shank portion.

* * * * *